US009801567B2

(12) United States Patent
Kuramoto et al.

(10) Patent No.: US 9,801,567 B2
(45) Date of Patent: Oct. 31, 2017

(54) MEDICAL IMAGE PROCESSING DEVICE, METHOD FOR OPERATING THE SAME, AND ENDOSCOPE SYSTEM

(71) Applicant: FUJIFILM Corporation, Tokyo (JP)

(72) Inventors: Masayuki Kuramoto, Ashigarakami-gun (JP); Makoto Sugizaki, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 301 days.

(21) Appl. No.: 14/814,234

(22) Filed: Jul. 30, 2015

(65) Prior Publication Data

US 2016/0029925 A1 Feb. 4, 2016

(30) Foreign Application Priority Data

Aug. 4, 2014 (JP) ................. 2014-158561

(51) Int. Cl.
*A61B 5/103* (2006.01)
*H04N 1/56* (2006.01)
(Continued)

(52) U.S. Cl.
CPC ........ *A61B 5/1032* (2013.01); *A61B 1/00009* (2013.01); *A61B 1/0646* (2013.01);
(Continued)

(58) Field of Classification Search
CPC ... A61B 5/1032; A61B 1/00009; A61B 1/041;
A61B 1/05; A61B 1/0646; A61B 1/0653;
A61B 1/0684; A61B 1/2736; G06T
7/0012; G06T 7/408; G06T 2207/10024;
G06T 2207/10068; G06T 2207/30092;
(Continued)

(56) References Cited

U.S. PATENT DOCUMENTS

2003/0152285 A1* 8/2003 Feldmann ................ H04N 9/75
382/274
2011/0274350 A1* 11/2011 Hara ......................... G06T 5/20
382/167
2013/0216131 A1* 8/2013 Free ....................... H04N 9/643
382/165

FOREIGN PATENT DOCUMENTS

JP 63-173182 A 7/1988
JP 3228627 B2 11/2001

OTHER PUBLICATIONS

Japanese Office Action, dated Nov. 2, 2016, for Japanese Application No. 2014-158561, along with an English machine translation.

* cited by examiner

*Primary Examiner* — Edward Park
(74) *Attorney, Agent, or Firm* — Birch, Stewart, Kolasch & Birch, LLP

(57) ABSTRACT

First RGB image signals are inputted. A first B/G ratio and a first G/R ratio are calculated. The first B/G ratio and the first G/R ratio are converted into a second B/G ratio and a second G/R ratio, respectively, through a color information conversion process. Owing to the color information conversion process, a difference between first and second observation areas in a second signal ratio space formed by the second B/G ratio and the second G/R ratio is greater than a difference between the first and second observation areas in a first signal ratio space formed by the first B/G ratio and the first G/R ratio, and a difference between the first and third observation areas in the second signal ratio space is greater than a difference between the first and third observation areas in the first signal ratio space.

13 Claims, 37 Drawing Sheets

(A)

(B)

(51) Int. Cl.
*A61B 1/00* (2006.01)
*A61B 1/273* (2006.01)
*A61B 1/06* (2006.01)
*G06T 7/00* (2017.01)
*H04N 9/64* (2006.01)
*G06T 7/90* (2017.01)
*A61B 1/05* (2006.01)
*A61B 1/04* (2006.01)
*H04N 5/225* (2006.01)

(52) U.S. Cl.
CPC .......... *A61B 1/0653* (2013.01); *A61B 1/2736* (2013.01); *G06T 7/0012* (2013.01); *G06T 7/90* (2017.01); *H04N 1/56* (2013.01); *H04N 9/643* (2013.01); *A61B 1/041* (2013.01); *A61B 1/05* (2013.01); *A61B 1/0684* (2013.01); *G06T 2207/10024* (2013.01); *G06T 2207/10068* (2013.01); *G06T 2207/30092* (2013.01); *G06T 2207/30096* (2013.01); *H04N 2005/2255* (2013.01)

(58) Field of Classification Search
CPC ............ G06T 2207/30096; H04N 1/56; H04N 9/643; H04N 2005/2255
See application file for complete search history.

ab SPACE FORMED BY COLOR COMPONENTS a*, b* OF CIE Lab SPACE (A)                                                  (B)

ab SPACE FORMED BY COLOR COMPONENTS a*, b* OF CIE Lab SPACE ab SPACE FORMED BY COLOR COMPONENTS a*, b* OF CIE Lab SPACE (A)     (B)

(A)            (B)

(A)  (B)

(A)    (B)

US 9,801,567 B2

MEDICAL IMAGE PROCESSING DEVICE, METHOD FOR OPERATING THE SAME, AND ENDOSCOPE SYSTEM

CROSS-REFERENCE TO RELATED APPLICATIONS

The present application claims priority under 35 U.S.C. §119 to Japanese Patent Application No. 2014-158561, filed Aug. 4, 2014. Each of the above application(s) is hereby expressly incorporated by reference, in its entirety, into the present application.

BACKGROUND OF THE INVENTION

1. Field of the Invention

The present invention relates to a medical image processing device for producing an image in which a difference in color between a normal site and a lesion site is enhanced, a method for operating a medical image processing device, and an endoscope system.

2. Description Related to the Prior Art

In medical fields, diagnoses using endoscope systems have been widely performed. The endoscope system comprises a light source device, an endoscope, and a processor device. In the endoscope system, illumination light is applied from an endoscope to a region of interest (object), and the object under the illumination light is imaged with an imaging element of the endoscope. Based on an image signal obtained by imaging the object, an image of the object is displayed on a monitor. A doctor detects the presence or absence of a lesion while observing the image displayed on the monitor.

It is easy to detect a lesion (e.g. protrusion from mucosal surface) which significantly differs from a normal site (normal portion) in shape and size. However, in the case where a lesion is similar to the normal portion in shape and size, the lesion is detected based on a difference in color from that of the normal portion. It is extremely difficult to detect the lesion in a case where the lesion is in its early stage and there is little difference in color between the lesion and the normal portion.

In Japanese Patent No. 3228627, a difference in color between the normal portion and the lesion is made clearly visible by a process to further increase or decrease the value of a portion, which is deviated from a reference value of blood volume (hemoglobin index), to be away from the reference value.

It is known that gastric (stomach) cancer causes atrophy (decrease in size) of gastric mucosa (mucous membrane layer of the stomach), which makes the color of the gastric mucosa to fade. For this reason, there is a difference in color between the atrophic mucosa and the normal mucosa. The stomach cancer is diagnosed by checking the presence of the difference in color between the suspected lesion and the normal portion with an endoscope. "ABC method (ABC screening)" is recommended by the authorized nonprofit organization "Japan Research Foundation of Prediction, Diagnosis and Therapy for Gastric Cancer".

In advanced stages of atrophy (for example, groups C or D in the ABC screening), the difference in color between the normal portion and the atrophic portion is clear, so that it is easy to detect the atrophic portion. However, in intermediate stages (for example, groups B and C in the ABC screening), there is little difference in color between the atrophic portion and the normal portion, making it difficult to detect the atrophic portion based only on the difference in color. It is necessary to enhance the difference in color between the atrophic portion and the normal portion in an image, to facilitate the detection of the atrophic portion even if there is little difference in color between them.

Note that the difference in color between the atrophic portion and the normal portion in the image may be enhanced using a method described in the Japanese Patent No. 3228627. However, the color of the atrophic portion is affected not only by the blood volume but also by factors other than the blood volume. Therefore it is difficult to enhance the difference in color between the atrophic portion and the normal portion with the use of the method described in the Japanese Patent No. 3228627.

SUMMARY OF THE INVENTION

An object of the present invention is to provide a medical image processing device for producing an image in which a difference in color between an abnormal portion (e.g. an atrophic portion with atrophic gastric mucosa) and a normal portion is enhanced, a method for operating a medical image processing device, and an endoscope system.

A medical image processing device according to the present invention comprises an input processing unit, a color information obtaining section, and a color information converter. The input processing unit performs an input process of a first color image signal. The color information obtaining section obtains two or more pieces of first color information from the first color image signal. The color information converter performs a color information conversion process to convert the two or more pieces of first color information into two or more pieces of second color information. The color information conversion process makes a difference $D12y$ greater than a difference $D12x$ and makes a difference $13y$ greater than a difference $13x$. The difference $D12x$ is a difference between a first observation area and a second observation area that differs in position from the first observation area in a first feature space formed by the two or more pieces of first color information. The difference $D12y$ is a difference between the first and second observation areas in a second feature space formed by the two or more pieces of second color information. The difference $D13x$ is a difference between the first observation area and a third observation area that differs in position from the first and second observation areas in the first feature space. The difference $D13y$ is a difference between the first and third observation areas in the second feature space.

It is preferred that the color information converter has a first color information converter for performing a first color information conversion process as the color information conversion process. The first color information conversion process makes at least one of saturation and hue of the first observation area in the second feature space different from at least one of saturation and hue of the first observation area in the first feature space.

It is preferred that the difference $D12x$ before the first color information conversion process represents a difference in saturation, and the difference $D13x$ before the first color information conversion process represents a difference in hue. It is preferred that the difference $D12y$ after the first color information conversion process represents differences in saturation and hue, and the difference $D13y$ after the first color information conversion process represents a difference in hue.

It is preferred that the color information converter has a second color information converter for performing a second color information conversion process as the color information conversion process, and the second color information conversion process makes the first observation area in the second feature space identical in saturation and hue to the first observation area in the first feature space.

It is preferred that the difference $D12x$ before the second color information conversion process represents a difference in saturation, and the difference $D13x$ before the second color information conversion process represents a difference in hue. It is preferred that the difference $D12y$ after the second color information conversion process represents a difference in saturation, and the difference $D13y$ after the second color information conversion process represents a difference in hue.

It is preferred that the first color image signal is image signals of three colors, and the two or more pieces of first color information are a first signal ratio Mx, between the two image signals out of the image signals of three colors, and a first signal ratio Nx, between the two image signals out of the image signals of three colors, different from the first signal ratio Mx. The color information converter performs the color information conversion process to convert the first signal ratio Mx and the first signal ratio Nx into a second signal ratio My and a second signal ratio Ny, being the two or more pieces of second color information.

It is preferred that the two or more pieces of first color information are first color difference signals Cr_x and Cb_x, and the color information converter performs the color information conversion process to convert the first color difference signals Cr_x and Cb_x into second color difference signals Cr_y and Cb_y, being the two or more pieces of second color information.

It is preferred that the two or more pieces of first color information are first components a*_x and b*_x, being color components in a CIE Lab space, and the color information converter performs the color information conversion process to convert the first components a*_x and b*_x into second components a*_y and b*_y, being the two or more pieces of second color information.

It is preferred that the two or more pieces of first color information are a first hue H_x and a first saturation S_x, and the color information converter performs the color information conversion process to convert the first hue H_x and the first saturation S_x into a second hue H_y and a second saturation S_y, being the two or more pieces of second color information.

It is preferred that the medical image processing device further comprises a color image signal converter and a brightness adjuster. The color image signal converter converts the two or more pieces of second color information into a second color image signal. The brightness adjuster adjusts a pixel value of the second color image signal based on first brightness information obtained from the first color image signal and second brightness information obtained from the second color image signal.

It is preferred that the first color image signal is image signals of three colors. It is preferred that a difference $D12n$ between the first and second observation areas in the first feature space, for a case in which at least one of the image signals is a narrowband signal, is greater than a difference $D12b$ between the first and second observation areas in the first feature space, for a case in which all of the image signals are broadband signals, or a difference $D13n$ between the first and third observation areas in the first feature space, for the case in which at least one of the image signals is a narrowband signal, is greater than a difference $D13b$ between the first and third observation areas in the first feature space, for the case in which all of the image signals are broadband signals.

An endoscope system comprises the above-described medical image processing device and a display section. The display section displays a first special image and a second special image. The first special image is produced based on the two or more pieces of second color information obtained by the first color information conversion process. The second special image is produced based on the two or more pieces of second color information obtained by the second color information conversion process.

A method for operating a medical image processing device comprises an input processing step, a color information obtaining step, and a conversion processing step. In the input processing step, an input processing unit performs an input process of a first color image signal. In the color information obtaining step, a color information obtaining section obtains two or more pieces of first color information from the first color image signal. In the conversion processing step, a color information converter performs a color information conversion process to convert the two or more pieces of first color information into two or more pieces of second color information. The color information conversion process makes a difference $D12y$ greater than $D12x$ and makes a difference $13y$ greater than a difference $13x$. The difference $D12x$ is a difference between a first observation area and a second observation area that differs in position from the first observation area in a first feature space formed by the two or more pieces of first color information. The difference $D12y$ is a difference between the first and second observation areas in a second feature space formed by the two or more pieces of second color information. The difference $D13x$ is a difference between the first observation area and a third observation area that differs in position from the first and second observation areas in the first feature space. The difference $D13y$ is a difference between the first and third observation areas in the second feature space.

According to the present invention, an image in which a difference in color between an abnormal portion (e.g. an atrophic portion with an atrophic gastric mucosa) and a normal portion is enhanced is produced.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
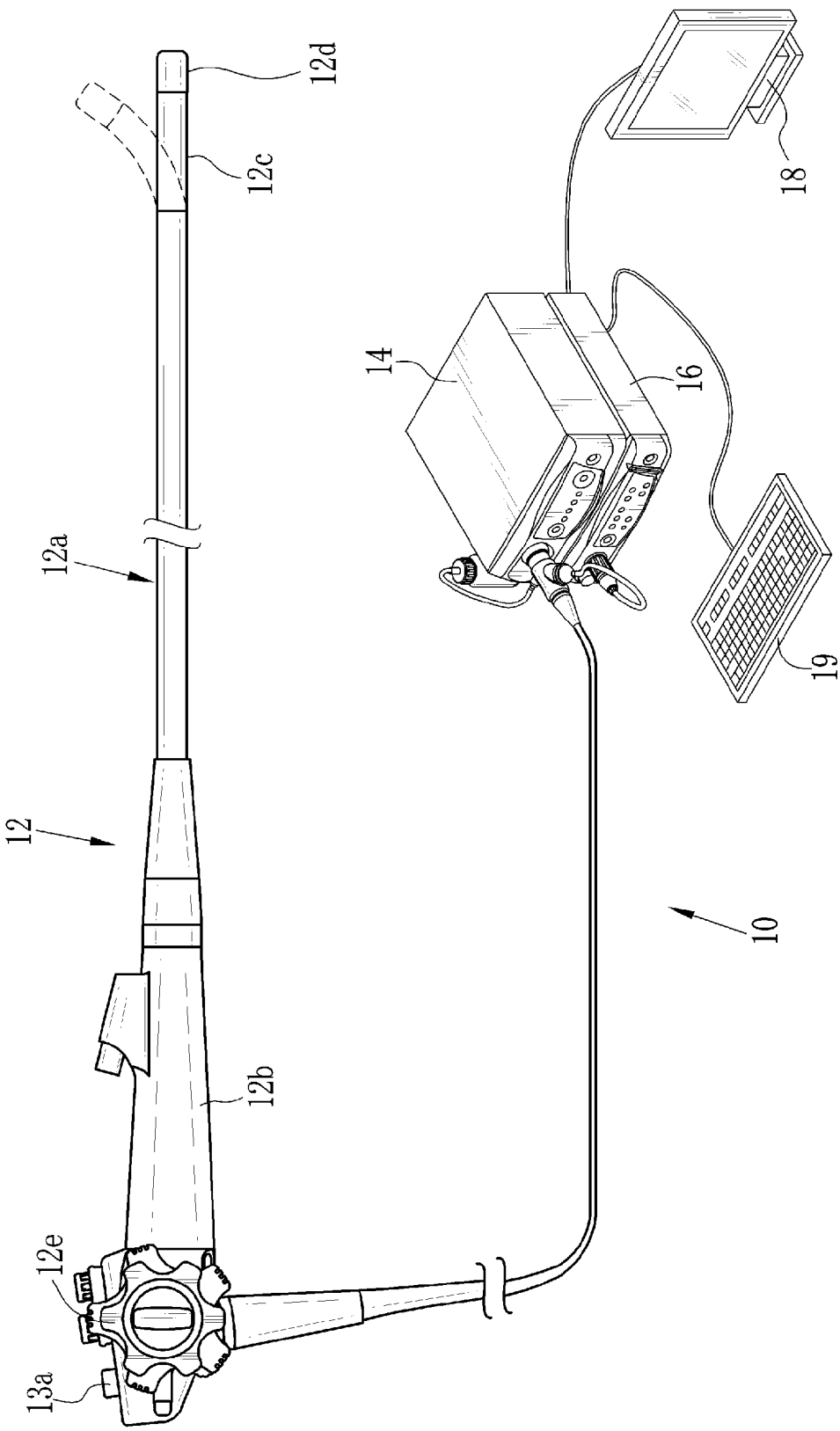
FIG. 1 is an external view of an endoscope system according to a first embodiment.

As illustrated in FIG. 1, an endoscope system 10 of a first embodiment comprises an endoscope 12, a light source device 14, a processor device 16, a monitor (display section) 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is provided on the distal side of the insertion section 12a. The flexible portion 12c is bent by operating an angle knob 12e of the control handle unit 12b. The distal portion 12d is directed to a desired direction by bending the flexible portion 12c.

The control handle unit 12b is provided with the angle knob 12e and a mode switch (SW) 13a. The mode SW 13a is operated to switch among four modes: a normal mode, a first special mode, a second special mode, and a simultaneous display mode. In the normal mode, a normal image is displayed on the monitor 18. The first special mode is used to examine a boundary between an atrophic portion and a normal portion. The atrophic portion refers to a portion, of gastric mucosa (mucous membrane layer of the stomach), with atrophy (shrinkage in the lining of stomach) caused by a lesion such as stomach cancer. In the first special mode, a first special image is displayed on the monitor 18. The second special mode is used to examine a difference in color between the atrophic portion and the normal portion. In the second special mode, a second special image is displayed on the monitor 18. The simultaneous display mode is used to examine the boundary between the atrophic portion and the normal portion and the difference in color between the atrophic portion and the normal portion at a time. In the simultaneous display mode, the first and second special images are displayed simultaneously or at a time on the monitor 18.

The processor device 16 is electrically connected to the monitor 18 and the console 19. The monitor 18 outputs and displays image information and the like. The console 19 functions as a UI (user interface), which receives input operation such as setting a function. Note that an external storage unit (not shown) for recording the image information and the like may be connected to the processor device 16.

Figure 2:
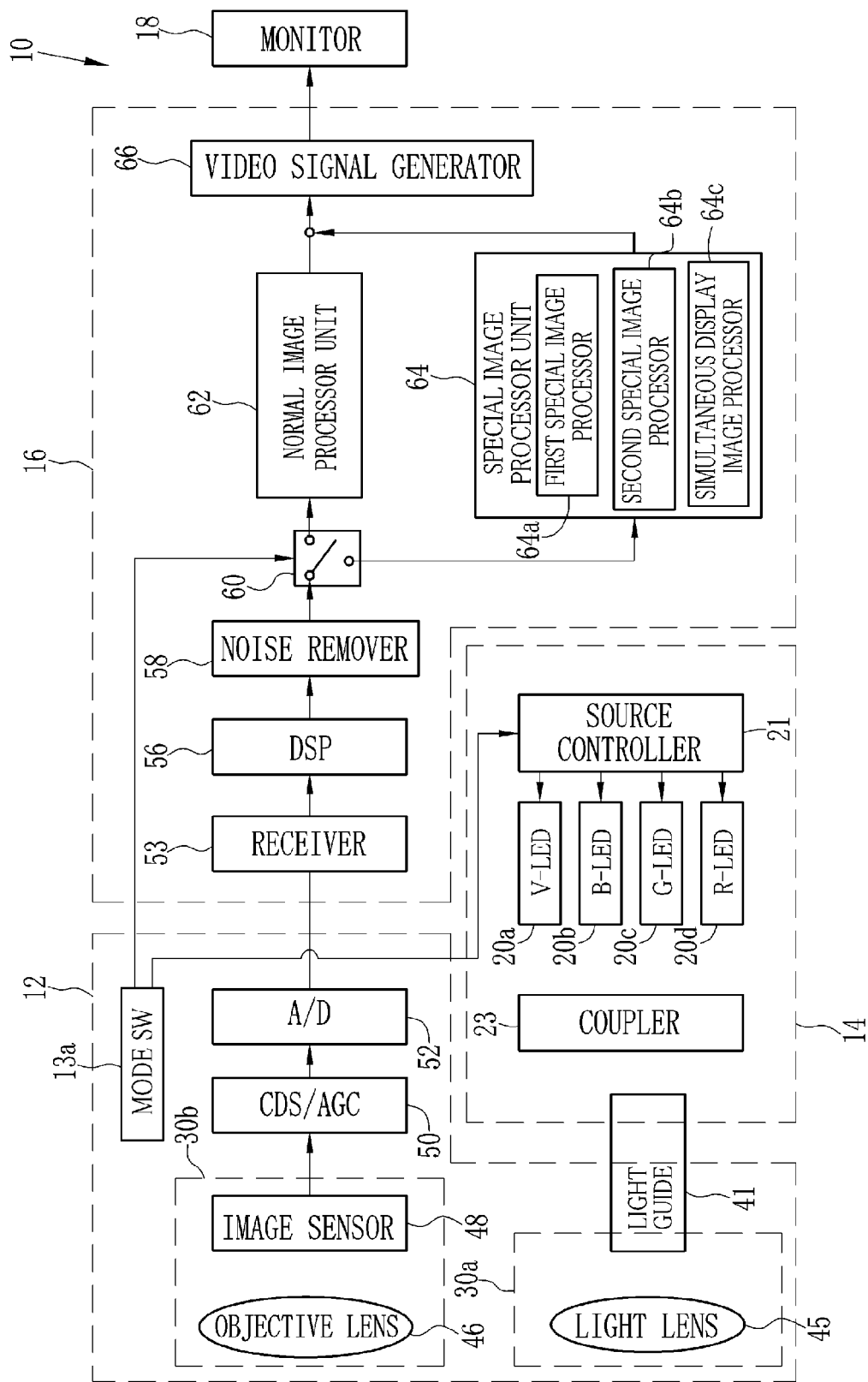
FIG. 2 is a block diagram illustrating functions of the endoscope system according to the first embodiment.

As illustrated in FIG. 2, the light source device 14 comprises a V-LED (Violet Light Emitting Diode) 20a, a B-LED (Blue Light Emitting Diode) 20b, a G-LED (Green Light Emitting Diode) 20c, an R-LED (Red Light Emitting Diode) 20d, a source controller 21 for controlling the LEDs 20a to 20d, and a combiner 23. The combiner 23 combines the optical paths of four colors of light from the four colors of LEDs 20a to 20d together. The light combined by the combiner 23 is applied to the object in a body cavity through a light guide (LG) 41 and a light lens 45. The light guide 41 extends inside the insertion section 12a. Note that an LD (Laser Diode) may be used in place of the LED.

Figure 3:
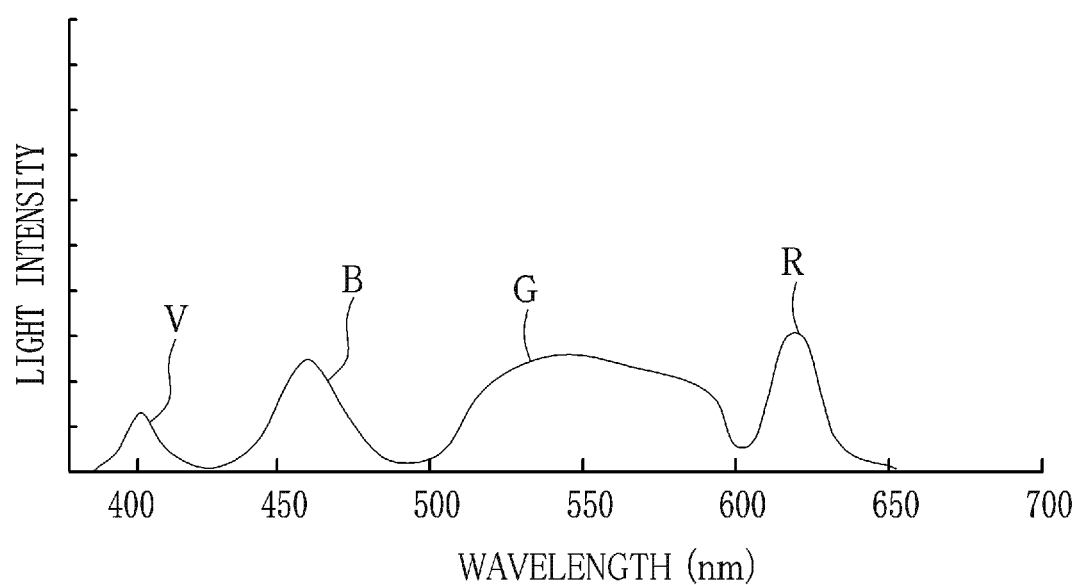
FIG. 3 is a graph illustrating emission spectrums of violet light V, blue light B, green light G, and red light R.

As illustrated in FIG. 3, the V-LED 20a generates violet light V having a wavelength range of 380 to 420 nm and the center wavelength 405±10 nm. The B-LED 20b generates blue light B having a wavelength range of 420 to 500 nm and the center wavelength 460±10 nm. The G-LED 20c generates green light G having a wavelength range of 480 to 600 nm. The R-LED 20d generates red light R having a wavelength range of 600 to 650 nm and the center wavelength 620-630 nm.

In each of the normal mode, the first special mode, the second special mode, and the simultaneous display mode, the source controller 21 turns on the V-LED 20a, the B-LED 20b, the G-LED 20c, and the R-LED 20d. In other words, the mixture of the violet light V, the blue light B, the green light G, and the red light R is applied to the object. In the normal mode, the source controller 21 controls the LEDs 20a to 20d to make a light quantity ratio among the violet light V, the blue light B, the green light G, and the red light R to be Vc:Bc:Gc:Rc. In the first and second special modes and the simultaneous display mode, the source controller 21 controls the LEDs 20a to 20d to make the light quantity ratio among the violet light V, the blue light B, the green light G, and the red light R to be Vs:Bs:Gs:Rs.

As illustrated in FIG. 2, the light guide 41 is incorporated in the endoscope 12 and a universal code that connects the endoscope 12, the light source device 14, and the processor device 16. The light guide 41 transmits the light combined by the combiner 23 to the distal portion 12d of the endoscope 12. Note that a multimode fiber may be used as the light guide 41. For example, a small-diameter fiber cable with the core diameter 105 μm, the clad diameter 125 μm, and the outer diameter φ 0.3 to 0.5 mm (including a protection layer, being a jacket) may be used.

The distal portion 12d of the endoscope 12 comprises an illumination optical system 30a and an imaging optical system 30b. The illumination optical system 30a has the light lens 45. The light from the light guide 41 is applied to the object through the light lens 45. The imaging optical system 30b has an objective lens 46 and an image sensor 48. The light reflected from the object is incident on the image sensor 48 through the objective lens 46. Thereby a reflection image of the object is formed on the image sensor 48.

The image sensor 48 is a color image sensor. The image sensor 48 captures the reflection image of the object, and outputs an image signal. It is preferred that the image sensor 48 is a CCD (Charge Coupled Device) image sensor, a CMOS (Complementary Metal-Oxide Semiconductor) image sensor, or the like. The image sensor 48 used in the present invention is a color image sensor for obtaining image signals of three colors, R (red), G (green), and B (blue), that is, a so-called RGB image sensor comprising R pixels with R filters, G pixels with G filters, and B pixels with B filters.

Note that the image sensor 48 may be a so-called complementary color image sensor instead of the RGB image sensor. The complementary color image sensor has complementary color filters of C (cyan), M (magenta), Y (yellow), and G (green). In the case where the complementary color image sensor is used, four colors (CMYG) of image signals are outputted. It is necessary to convert the four colors (CMYG) of image signals into three colors (RGB) of image signals through complementary color/primary color conversion. Alternatively, the image sensor 48 may be a monochrome image sensor with no color filters. In this case, it is necessary that the source controller 21 allows emitting the blue light B, the green light G, and the red light R in a time-division manner. It is also necessary to add a synchronization process in processing the image signals.

The image signal outputted from the image sensor 48 is transmitted to a CDS/AGC circuit 50. The CDS/AGC circuit 50 performs correlated double sampling (CDS) and automatic gain control (AGC) on the image signal, being an analog signal. The image signal which has passed through the CDS/AGC circuit 50 is then converted into a digital image signal by an A/D converter 52. The digital image signal is inputted to the processor device 16.

The processor device 16 comprises a receiver 53, a DSP (Digital Signal Processor) 56, a noise remover 58, an image processing selector 60, a normal image processor unit 62, a special image processor unit 64, and a video signal generator 66. The receiver 53 receives the digital RGB image signals from the endoscope 12. The R image signal corresponds to the signals outputted from the R pixels of the image sensor 48. The G image signal corresponds to the signals outputted from the G pixels of the image sensor 48. The B image signal corresponds to the signals outputted from the B pixels of the image sensor 48.

The DSP 56 performs various types of signal processing (defect correction process, offset processing, gain correction process, linear matrix processing, gamma conversion process, demosaicing process, and the like) on the image signal received. In the defect correction process, signals from defective pixels in the image sensor 48 are corrected. In the offset processing, dark current components are removed from the RGB image signals which have been subjected to the defect correction process. Thereby an accurate zero level is set. In the gain correction process performed after the offset processing, a signal level is adjusted or corrected by multiplying the RGB image signals by a specific gain. After the gain correction process, the RGB image signals are subjected to the linear matrix processing to increase color reproducibility. Thereafter, brightness and saturation are adjusted or corrected through the gamma conversion process. After the linear matrix processing, the RGB image signals are subjected to the demosaicing process (also referred to as equalization process) in which color signal(s) lacking in each pixel is generated by interpolation. Owing to the demosaicing process, each pixel has three colors (RGB) of signals.

The DSP 56 performs gamma correction and the like on the RGB image signals. Thereafter, the noise remover 58 removes noise from the RGB image signals through a noise removing process (for example, moving average method or median filter method). Then, the RGB image signals are transmitted to the image processing selector 60. Note that "input processing unit" of the present invention corresponds to the configuration comprising the receiver 53, the DSP 56, and the noise remover 58.

In the case of the normal mode set by operating the mode SW 13*a*, the image processing selector 60 transmits the RGB image signals to the normal image processor unit 62. In the case of the first special mode, the second special mode, or the simultaneous display mode, the image processing selector 60 transmits the RGB image signals to the special image processor unit 64.

The normal image processor unit 62 performs color conversion process, color enhancement process, and structure enhancement process on the RGB image signals. In the color conversion process, the digital RGB image signals are subjected to 3×3 matrix processing, tone conversion process, three-dimensional LUT process, and the like. Thereby the digital RGB image signals are converted into the color-converted RGB image signals. Next, the color-converted RGB image signals are subjected to various types of color enhancement processes. The color-enhanced RGB image signals are subjected to the structure enhancement process (e.g. spatial frequency enhancement and the like). The structure-enhanced RGB image signals are inputted as the RGB image signals of the normal image from the normal image processor unit 62 to the video signal generator 66.

The special image processor unit 64 operates when the mode is set to the first special mode, the second special mode, or the simultaneous display mode. The special image processor unit 64 comprises a first special image processor 64*a* for producing a first special image, a second special image processor 64*b* for producing a second special image, and a simultaneous display image processor 64*c* for producing a special image used for displaying the first and second special images simultaneously or at a time. The first special image processor 64*a* does not produce the second special image. The second special image processor 64*b* does not produce the first special image. The first special image processor 64*a*, the second special image processor 64*b*, and the simultaneous display image processor 64*c* will be described in detail below. The RGB image signals of the first special image, the second special image, or the special image for simultaneous display, which are generated in the special image processor unit 64, are inputted to the video signal generator 66.

The video signal generator 66 converts the RGB image signals, which are inputted from the normal image processor unit 62 or the special image processor unit 64, into a video signal to be displayed as an image on the monitor 18. Based on the video signal, the monitor 18 displays the normal image, the first special image, or the second special image, or the first and second special images simultaneously or at a time.

Figure 4:
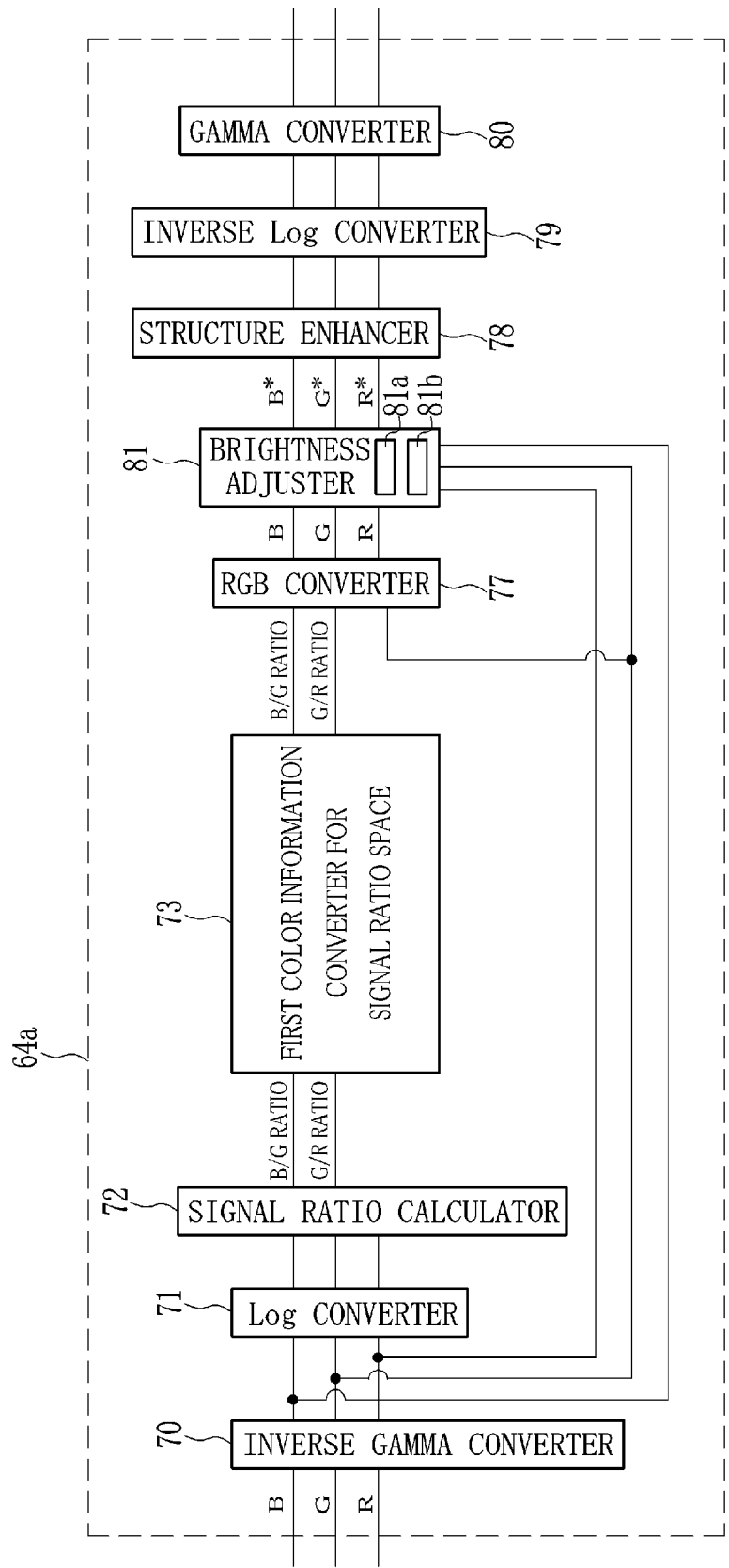
FIG. 4 is a block diagram illustrating functions of a first special image processor.

As illustrated in FIG. 4, the first special image processor 64*a* comprises an inverse gamma converter 70, a log converter 71, a signal ratio calculator 72, a first color information converter 73 (for the signal ratio space), an RGB converter 77, a structure enhancer 78, an inverse log converter 79, and a gamma converter 80. The first special image processor 64*a* also comprises a brightness adjuster 81 between the RGB converter 77 and the structure enhancer 78.

The inverse gamma converter 70 performs inverse gamma conversion on the inputted RGB image signals. The RGB image signals after the inverse gamma conversion are linearly-changing RGB signals, which change linearly relative to reflectance from the object. Owing to this, proportions of the signal components related to various types of biological information increase in the RGB image signals. Note that the linearly-changing R image signal is referred to as a first R image signal. The linearly-changing G image signal is referred to as a first G image signal. The linearly-changing B image signal is referred to as a first B image signal.

The log converter 71 performs log conversion of each of the first RGB image signals (which correspond to "first color image signal" of the present invention). Thereby, a log-converted R image signal (log R), a log-converted G image signal (log G), and a log-converted B image signal (log B) are obtained. The signal ratio calculator 72 (which corresponds to a "color information obtaining section" of the present invention) performs difference processing (log G−log B=log G/B=−log(B/G)) based on the log-converted G image signal and the log-converted B image signal. Thereby, a first B/G ratio (which corresponds to "first signal ratio Mx" of the present invention) is calculated. Here, the first B/G ratio refers to −log(B/G) with the "−log" omitted. The signal ratio calculator 72 performs difference processing (log R−log G=log R/G=−log(G/R)) based on the log-converted R image signal and the log-converted G image signal. Thereby, a first G/R ratio (which corresponds to "first signal ratio Nx" of the present invention) is calculated. The first G/R ratio refers to −log (G/R) with the "−log" omitted in a manner similar to the first B/G ratio. Hereinafter, a two-dimensional color space formed by the first B/G ratio and the first G/R ratio is referred to as "first signal ratio space", which corresponds to "first feature space" of the present invention.

Note that the first B/G ratio and the first G/R ratio are calculated with respect to the pixels in the same positions in the first B image signal, the first G image signal, and the first R image signal. The first B/G ratio and the first G/R ratio are calculated for each pixel. The first B/G ratio correlates with a blood vessel depth (distance between the mucosal surface and a position of a specific blood vessel), so that the first B/G ratio varies with the blood vessel depth. The first G/R ratio correlates with the blood volume (hemoglobin index), so that the first G/R ratio varies with the blood volume.

The first color information converter 73 (for the signal ratio space) performs a first color information conversion process (for the signal ratio space) on the first B/G ratio and the first G/R ratio, which are calculated by the signal ratio calculator 72, to convert the first B/G ratio and the first G/R ratio into a second B/G ratio and a second G/R ratio. The second B/G ratio corresponds to a "second signal ratio My" of the present invention. The second G/R ratio corresponds to a "second signal ratio Ny" of the present invention. The first color information converter 73 (for the signal ratio space) is composed of a two-dimensional LUT (Look Up Table), in which the first B/G ratio, the first G/R ratio, the second B/G ratio, and the second G/R ratio are stored in association with each other. The second B/G ratio and the second G/R ratio are obtained by the first color information conversion process which is performed based on the first B/G ratio and the first G/R ratio. The first color information conversion process will be detailed below.

Figure 5:
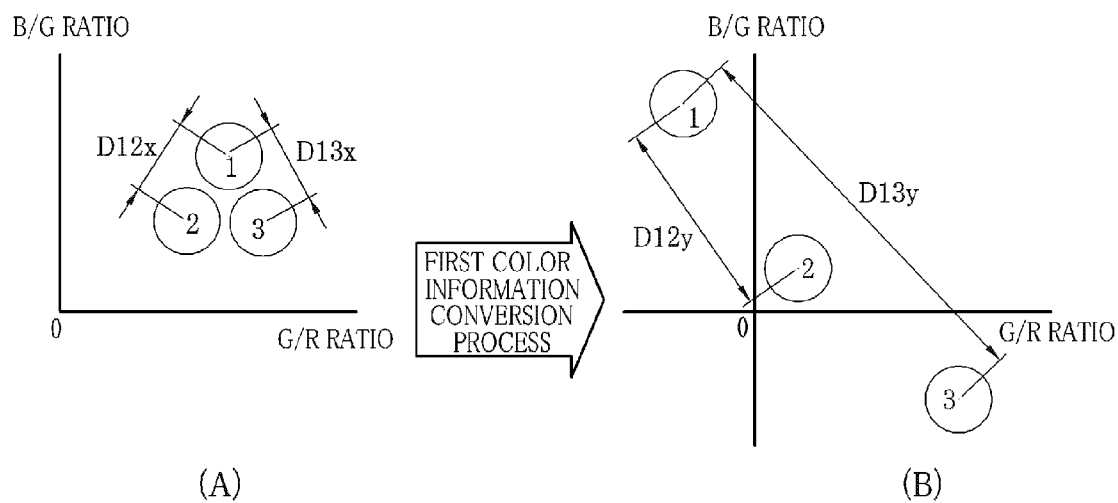
FIG. 5 is an explanatory view illustrating a first color information conversion process for a signal ratio space.

As illustrated in the part (A) of FIG. 5, in the first signal ratio space formed by the first B/G ratio (vertical axis) and the first G/R ratio (horizontal axis), a first observation area, a second observation area, and a third observation area are in the first quadrant. In the first observation area, normal mucosa is distributed. In the second observation area, atrophic mucosa caused by atrophic gastritis (thinning of the lining of the stomach) is distributed. The third observation area is located beneath the atrophic mucosa caused by the atrophic gastritis, and deep blood vessels are distributed in the third observation area. The deep blood vessels in the third observation area are seen through the atrophic mucosa as the atrophy progresses. In the first signal ratio space, there is a difference (distance) D12$x$ between the first and second observation areas (for example, between the average value of the first observation area and the average value of the second observation area). There is a difference (distance) D13$x$ between the first and third observation areas (for example, between the average value of the first observation area and the average value of the third observation area) The difference D12$x$ represents a difference in saturation between colors in the first observation area and colors in the second observation area in the image. The difference D13$x$ represents a difference in hue between the colors in the first observation area and colors in the third observation area in the image.

Note that in the part (A) of FIG. 5, "1" denotes the "first observation area"; "2" denotes the "second observation area"; and "3" denotes the "third observation area" (the same hereinafter) In the part (A) of FIG. 5, the term "first" of the "first B/G ratio" (the vertical axis) and the term "first" of the "first G/R ratio" (horizontal axis) are omitted (the same hereinafter).

As illustrated in the part (B) of FIG. 5, the first, second, and third observation areas are distributed in a second signal ratio space formed by the second B/G ratio (the vertical axis) and the second G/R ratio (the horizontal axis), which are obtained by the first color information conversion process (for the signal ratio space). In the second signal ratio space, which corresponds to a "second feature space" of the present invention, there is a difference (distance) D12$y$ between the first and second observation areas (for example, between the average value of the first observation area and the average value of the second observation area). There is a difference D13$y$ between the first and third observation areas (for example, between the average value of the first observation area and the average value of the third observation area). In the part (B) of FIG. 5, the term "second" of the "second B/G ratio" (the vertical axis) and the term "second" of the "second G/R ratio" (horizontal axis) are omitted (the same hereinafter.

The difference D12$y$ represents differences in saturation and hue between the colors in the first observation area and the colors in the second observation area in the image. The difference D12$y$ is greater than the difference D12$x$. The difference D13$y$ represents a difference in hue between the colors in the first observation area and the colors in the third observation area in the image. The difference D13$y$ is greater than the difference D13$x$. Furthermore, the coordinates corresponding to the first observation area in the second signal ratio space differ from the coordinates corresponding to the first observation area in the first signal ratio space. In other words, at least one of the saturation and the hue of the first observation area after the first color information conversion process (for the signal ratio space) differs from that before the first color information conversion process.

As described above, the difference between the first and second observation areas and the difference between the first and third observation areas are increased by the first color information conversion process (for the signal ratio space) and at least one of the saturation and the hue of the first observation area after the first color information conversion process differs from that before the first color information conversion process. As a result, in the first special image produced based on the second B/G ratio and the second G/R ratio, which have been subjected to the first color information conversion process (for the signal ratio space), a boundary between the atrophic portion (the atrophic mucosa or the deep blood vessels located beneath and seen through the atrophic mucosa) and the normal portion (the normal mucosa) is displayed clearly.

Figure 6:
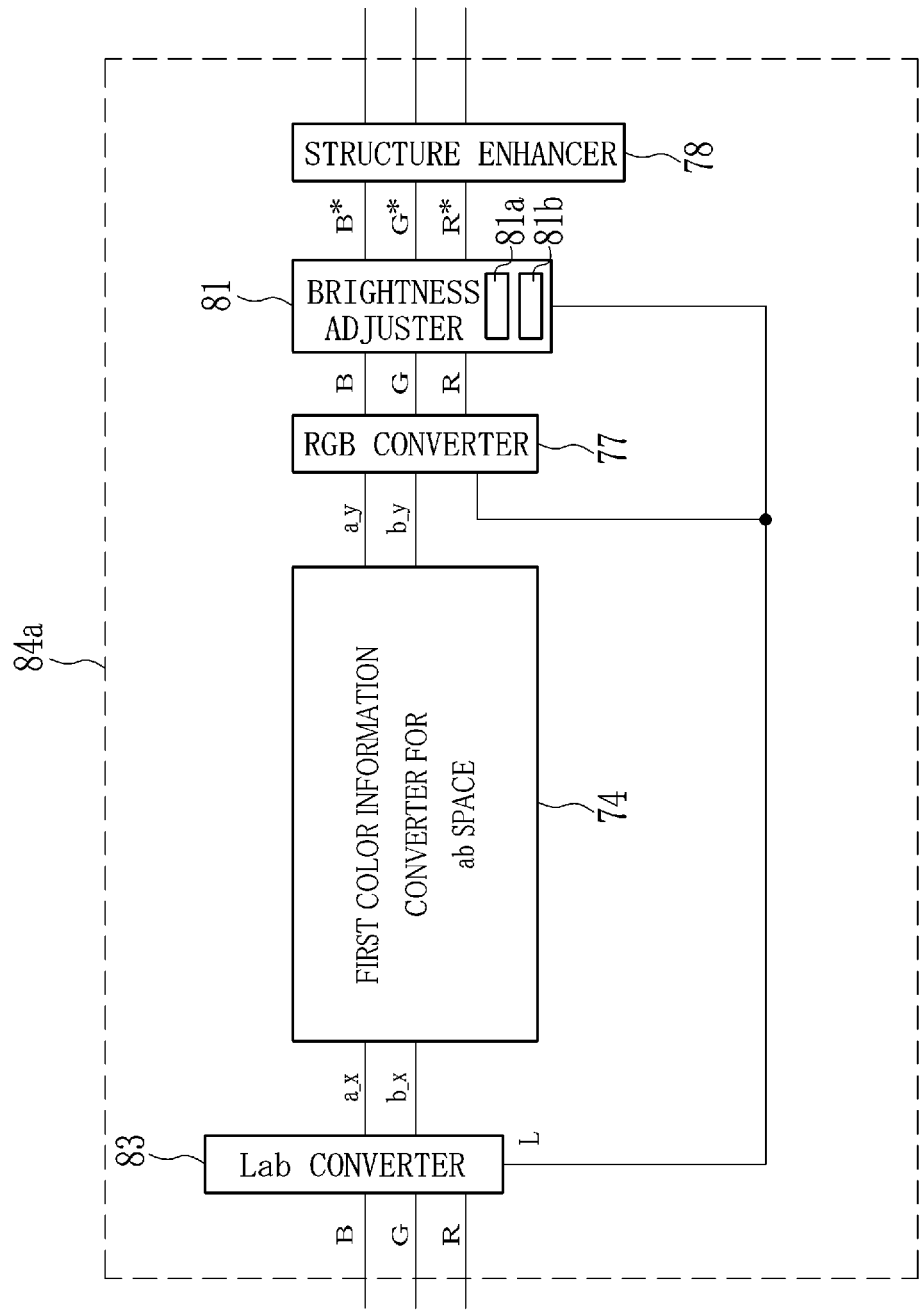
FIG. 6 is a block diagram illustrating functions of a first special image processor for an ab space.

Note that, in the case where the first color information conversion process (for an ab space) is performed with the use of a* and b*, a first special image processor 84$a$ (see FIG. 6) is used. Unlike the first special image processor 64$a$, the first special image processor 84$a$ is not provided with the inverse gamma converter 70, the log converter 71, the signal ratio calculator 72, the inverse log converter 79, and the gamma converter 80. Instead, the first special image processor 84$a$ comprises a Lab converter 83, which corresponds to the "color information obtaining section" of the present invention, and a first color information converter 74 (for the ab space). The components, other than those described above, of the first special image processor 84$a$ are the same as or similar to the components of the first special image processor 64$a$.

The Lab converter 83 converts the first RGB image signals into L and first components a*_x and b*_x (which are color components a* and b* in a CIE Lab space, the same hereinafter) through the well-known Lab conversion. The "L" is transmitted to the RGB converter 77 and the brightness adjuster 81. The first components a*_x and b*_x are transmitted to the first color information converter 74. The RGB converter 77 converts second components a*_y and b*_y, which have passed through the first color information converter 74, and "L" into second RGB image signals. A first brightness information calculator 81$a$ of the brightness adjuster 81 converts the "L", which is transmitted from the Lab converter 83, into a luminance signal Y with the use of a predetermined conversion equation. The converted luminance signal Y is referred to as first brightness information Yin. A second brightness information calculator 81$b$ calculates second brightness information Yout from the second RGB image signals. The brightness adjuster 81 uses the first brightness information Yin and the second brightness information Yout to adjust the pixel values of the second RGB image signals. Note that the method for calculating the second brightness information Yout and the method for adjusting the pixel values of the second RGB image signals are the same as or similar to those of the first special image processor 64$a$.

Figure 7:
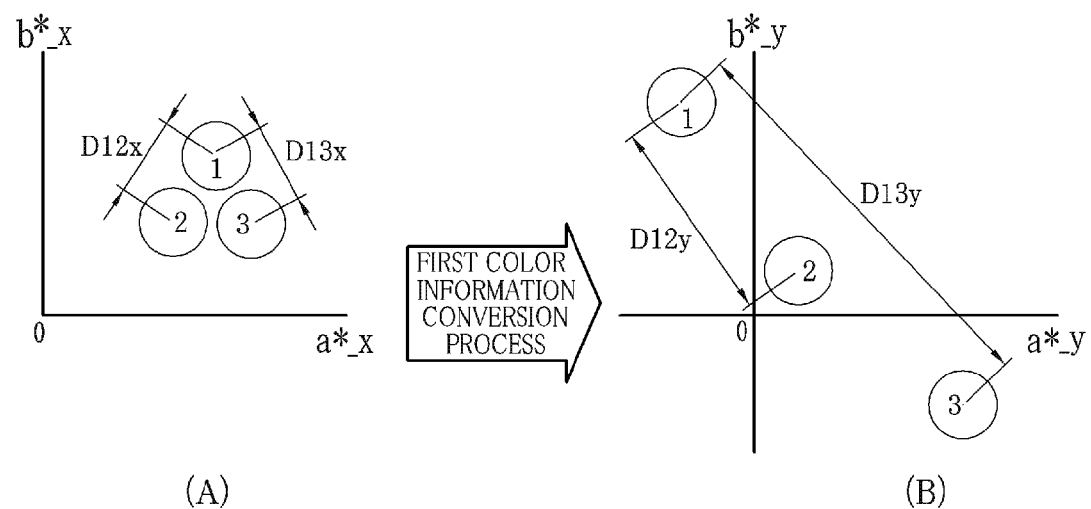
FIG. 7 is an explanatory view illustrating a first color information conversion process for the ab space.

Here, the part (A) of FIG. 7 illustrates the first to third observation areas in the first ab space formed by the first components a*_x and b*_x, the difference D12$x$ between the first and second observation areas, and the difference D13$x$ between the first and third observation areas. The part (B) of FIG. 7 illustrates the first to third observation areas in the second ab space formed by the second components a*_y and b*_y, which are obtained by the first color information conversion process (for the ab space), the difference D12$y$ between the first and second observation areas, and the difference D13$y$ between the first and third observation areas. As illustrated in FIG. 7, the difference between the first and second observation areas and the difference between the first and third observation areas are increased by the first color information conversion process (for the ab space). Note that the first ab space corresponds to the "first feature space" of the present invention. The second ab space corresponds to the "second feature space" of the present invention.

The RGB converter 77 (which corresponds to a "color image signal converter" of the present invention) uses at least one of the first RGB image signals to convert the second B/G and second G/R ratios, which have passed through the first color information converter 73 (for the signal ratio space), into the second RGB image signals (which correspond to "second color image signals" of the present invention). To convert the second B/G ratio into the second B image signal, the RGB converter 77 performs arithmetic operations based on the second B/G ratio and the first G image signal of the first RGB image signals, for example. To convert the second G/R ratio into the second R image signal, the RGB converter 77 performs arithmetic operations based on the second G/R ratio and the first G image signal of the first RGB image signals, for example. The RGB converter 77 outputs the first G image signal as a second G image signal, without any conversion.

The brightness adjuster 81 adjusts or corrects the pixel values of the second RGB image signals based on the first RGB image signals and the second RGB image signals. A reason for adjusting the pixel values of the second RGB image signals by the brightness adjuster 81 is as follows. Since the second RGB image signals are obtained by the first color information conversion process (for the signal ratio space) performed by the first color information converter 73 (for the signal ratio space), the brightness of the second RGB image signals may become significantly different from the brightness of the first RGB image signals. The brightness adjuster 81 adjusts the pixel values of the second RGB image signals to make the brightness of the second RGB image signals after the brightness adjustment equal to the brightness of the first RGB image signals.

The brightness adjuster 81 comprises the first brightness information calculator 81a and the second brightness information calculator 81b. The first brightness information calculator 81a calculates the first brightness information Yin based on the first RGB image signals. The second brightness information calculator 81b calculates the second brightness information Yout based on the second RGB image signals. The first brightness information calculator 81a calculates the first brightness information Yin with the use of an arithmetic expression "kr×pixel value of first R image signal+kg×pixel value of first G image signal+kb×pixel value of first B image signal". The second brightness information calculator 81b calculates the second brightness information Yout with the use of an arithmetic expression similar to that described above, in a manner similar to the first brightness information calculator 81a. After calculating the first brightness information Yin and the second brightness information Yout, the brightness adjuster 81 performs arithmetic operations based on the following expressions (E1) to (E3), thereby adjusting the pixel values of the second RGB image signals.

$$R^* = \text{pixel value of second } R \text{ image signal} \times Y\text{in}/Y\text{out} \quad (E1)$$

$$G^* = \text{pixel value of second } G \text{ image signal} \times Y\text{in}/Y\text{out} \quad (E2)$$

$$B^* = \text{pixel value of second } B \text{ image signal} \times Y\text{in}/Y\text{out} \quad (E3)$$

Note that "R*" denotes the second R image signal after the brightness adjustment. "G*" denotes the second G image signal after the brightness adjustment. "B*" denotes the second B image signal after the brightness adjustment. Each of "kr", "kg", and "kb" is an arbitrary constant within a range from 0 to 1.

The structure enhancer 78 performs the structure enhancement process on the second RGB image signals after the brightness adjustment by the brightness adjuster 81. The structure enhancement process may be frequency filtering or the like. The inverse log converter 79 performs inverse log conversion on the second RGB image signals which have passed through the structure enhancer 78. Thereby the second RGB image signals with antilogarithmic pixel values are obtained. The gamma converter 80 performs the gamma conversion on the second RGB image signals which have passed through the inverse log converter 79. Thereby the second RGB image signals with the tone suitable for an output device (e.g. the monitor 18) are obtained. The second RGB image signals which have passed through the gamma converter 80 are transmitted as the RGB image signals of the first special image to the simultaneous display image processor 64c or the video signal generator 66.

Figure 8:
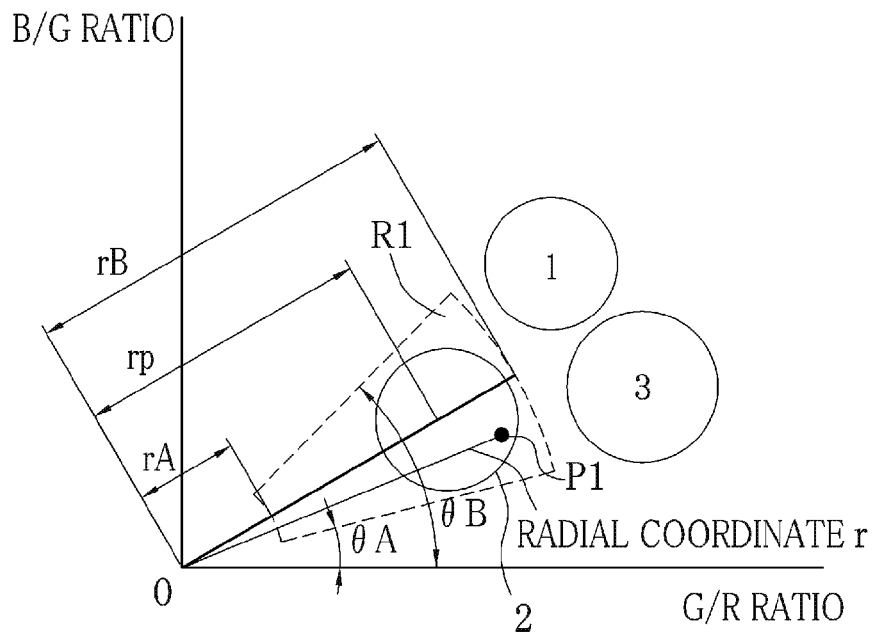
FIG. 8 is an explanatory view illustrating a first process.

The first color information conversion process (for the signal ratio space) is composed of a polar coordinate conversion process, first and second processes (for the signal ratio space), and a Cartesian coordinate conversion process. First, the first B/G ratio and the first G/R ratio, which are calculated by the signal ratio calculator 72, are converted into a radial coordinate r and an angular coordinate (angle) θ through the polar coordinate conversion process. Then, the first process (for the signal ratio space) is performed. As illustrated in FIG. 8, the radial coordinate r of the coordinates (point) P1 in a radial coordinate changing region R1 in the first signal ratio space is changed while the radial coordinate of the coordinates outside the radial coordinate changing region R1 is unchanged. In the radial coordinate changing region R1, the radial coordinate r takes a value between "rA" and "rB" and the angle θ takes a value between "θA" and "θB" (rA<rB, θA<θB). The radial coordinate changing region R1 is set to include the second observation area, in which the atrophic mucosa caused by the atrophic gastritis is distributed, and exclude the first observation area, in which the normal mucosa is distributed, and the third observation area, which is located beneath the atrophic mucosa and in which deep blood vessels seen through the atrophic mucosa are distributed.

Note that, in the first process (for the signal ratio space), the angular coordinate (angle) θ of the coordinates (point) in the radial coordinate changing region R1 is not changed. In the first process, it is preferred to perform an expansion process on the radial coordinate r which is within the range of "rp" to "rB" and to perform a compression process on the radial coordinate r which is within the range of "rA" to "rp". In the expansion process, the radial coordinate r is changed at a radial coordinate change ratio Vx, which is greater than "1". In the compression process, the radial coordinate r is changed at a radial coordinate change ratio Vy, which is less than 1. In the case where the radial coordinate change ratio is "1", note that the length of the radial coordinate r does not change even if the process for changing the radial coordinate r is performed.

Here, a radial coordinate change rate is represented by the inclination of a straight line "L1", being the tangent line of a curve CV1. The curve CV1 depicts the relationship between the radial coordinate r and the radial coordinate Er. The inclination of the straight line L1 is greater than "1" in the range of "rp" to "rB". On the other hand, the inclination of the straight line L1 is less than "1" in the range of "rA" to "rp" (see FIG. 9) The inclination of the straight line L1 outside the radial coordinate changing region R1 is "1" (see FIG. 9).

Figure 9:
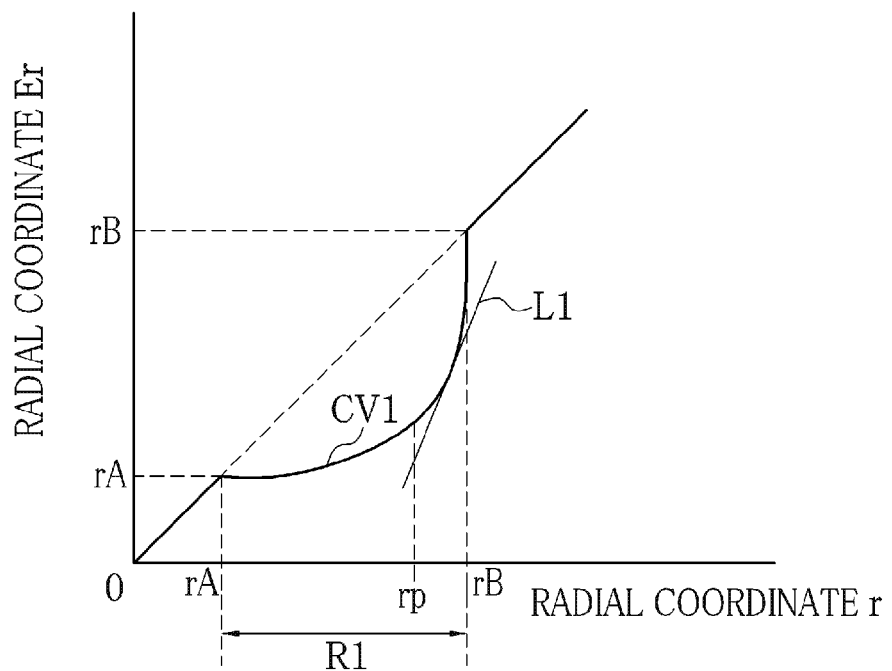
FIG. 9 is a graph illustrating a relationship between radial coordinate r and radial coordinate Er.

By the first process (for the signal ratio space), as illustrated in FIG. 9, the radial coordinate r in the radial coordinate changing region R1 is changed to the radial coordinate Er which is smaller than the radial coordinate r. The radial coordinate r located outside the radial coordinate changing region R1 is changed to the radial coordinate Er which is identical to the radial coordinate r (identical transformation).

Figure 10:
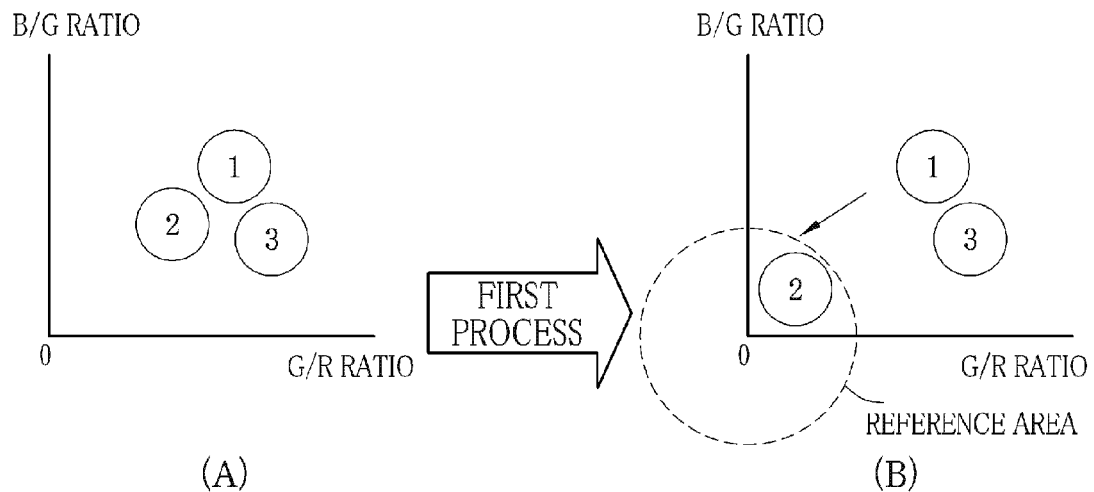
FIG. 10 is an explanatory view illustrating operation and effect of a first process for a signal ratio space.

As illustrated in the part (A) of FIG. 10, before the first process (for the signal ratio space), the first observation area, the second observation area, and the third observation area are close to each other. After the first process (for the signal ratio space), as illustrated in the part (B) of FIG. 10, only the coordinates of the second observation area are moved to a reference area containing the origin point while the coordinates of the first and third observation areas are maintained unchanged. The reference area refers to an area in which the saturation is low and which does not include the coordinates corresponding to the first and third observation areas obtained after the first process (for the signal ratio space).

Figure 11:
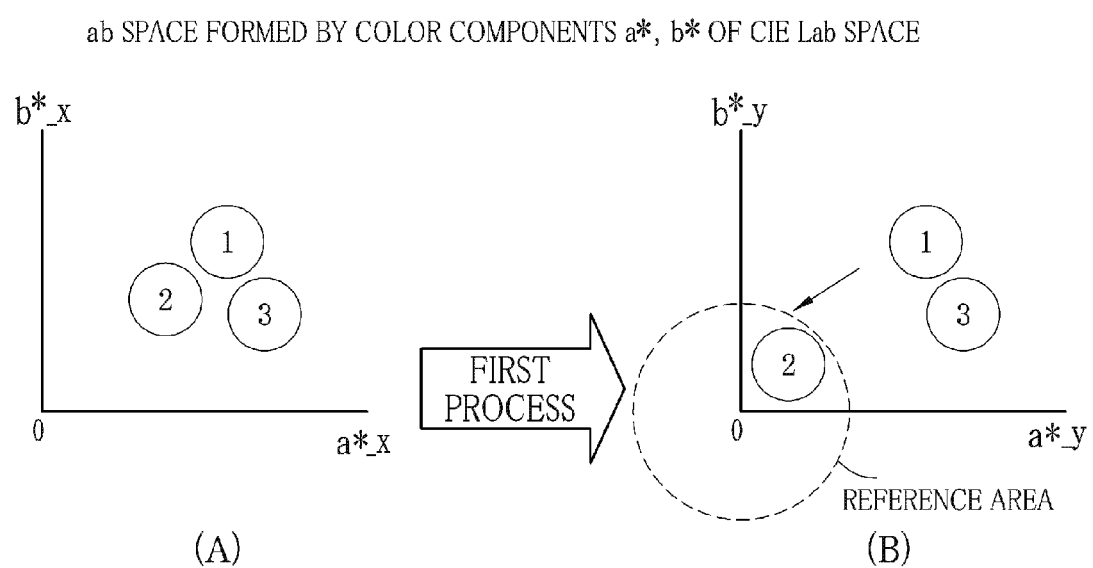
FIG. 11 is an explanatory view illustrating operation and effect of a first process for the ab space.

Note that, as illustrated in FIG. 11, in the case where the two or more pieces of first color information are the first components a*_x and b*_x, a first process (for the ab space) is performed in a like manner. In the first process, only the coordinates corresponding to the second observation area are moved to the reference area that contains the origin point while the coordinates corresponding to the first observation area and the coordinates corresponding to the third observation area are maintained unchanged. Here, the part (A) of FIG. 11 illustrates the distribution of the first to third observation areas before the first process (for the ab space). The part (B) of FIG. 11 illustrates the distribution of the first to third observation areas after the first process (for the ab space).

Figure 12:
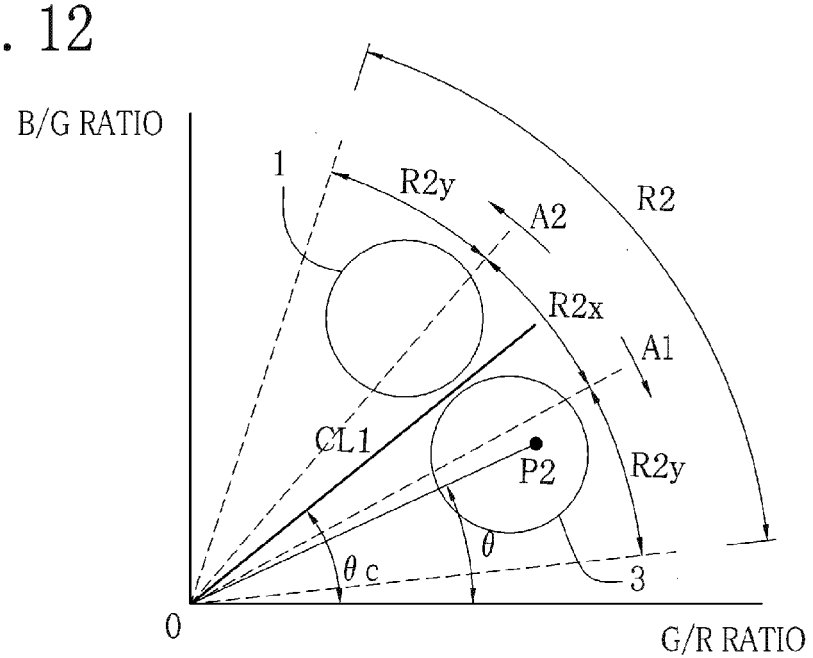
FIG. 12 is an explanatory view illustrating a second process for the signal ratio space.

In a second process (for the signal ratio space), as illustrated in FIG. 12, the angle θ of coordinates (point) P2 in an angle changing region R2 is changed while the angle θ of the coordinates (point) outside the angle changing region R2 is not changed. The angle changing region R2 is set to include the first observation area and the third observation area. Note that, in the second process (for the signal ratio space), the radial coordinate r of the coordinates (point) inside the angle changing region R2 is not changed.

Figure 13:
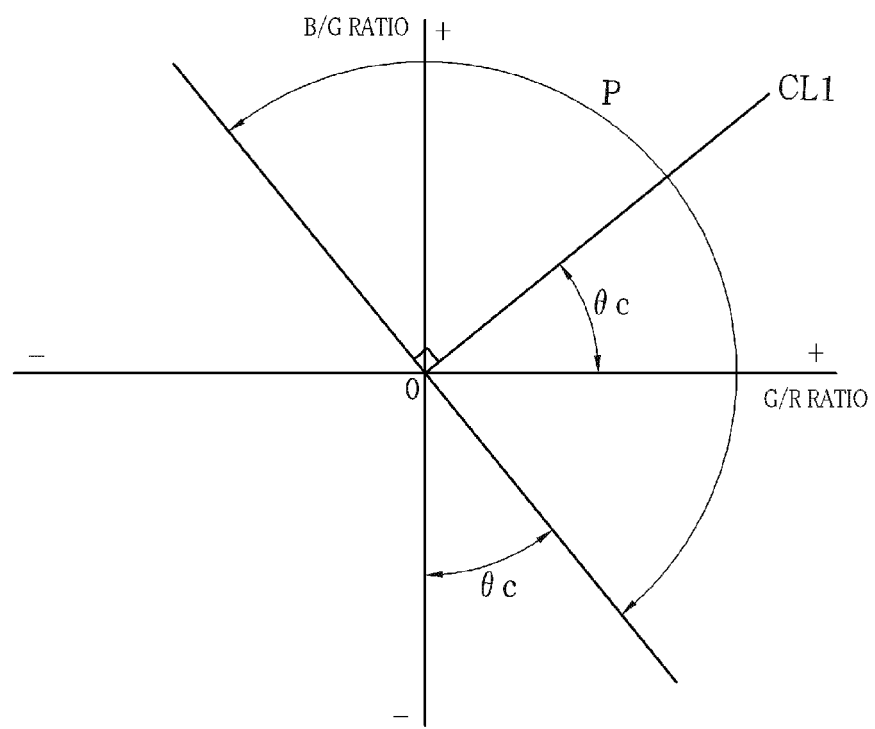
FIG. 13 is a graph illustrating a region within which the coordinates having an angle θ in an angle changing region R2 are to be moved.

In the angle changing region R2, a first center line CL1 is set between the first observation area and the third observation area. The first center line CL1 has an angle θc. In the second process (for the signal ratio space), the coordinates (point) with the angle (angular coordinate) θ which is smaller than the angle θc in the angle changing region R2 are rotated in the clockwise direction A1 while the coordinates (point) with the angle (angular coordinate) θ which is greater than the angle Sc in the angle changing region R2 are rotated in the counter clockwise direction A2. Note that, with regard to the angle θ which is within a range R2x extending from the first center line CL1, it is preferred to perform the expansion process for changing the angle θ at an angle change rate Wx, which is greater than "1". With regard to the angle θ which is within a range R2y outside the range R2x, it is preferred to perform the compression process for changing the angle θ at an angle change rate Wy, which is less than "1". It is preferred to move the coordinates, which are located in the angle changing region R2, within a region extending +90° (degrees) from the first center line CL1 (e.g. a region P extending from "270°+θc" to "θc+90°" in the case where the "positive" horizontal axis is 0° and an angle is expressed in degree from 0° to 360° in the signal ratio space (see FIG. 13)) through the second process (for the signal ratio space). Note that in a case where the angle change rate is "1", the angle θ does not change when subjected to the process for changing the angle θ.

Here, an angle change rate is represented by the inclination of a straight line "L2", being the tangent line of a curve CV2. The curve CV2 depicts the relationship between angles θ and Eθ. The inclination of the straight line L2 is greater than "1" in the range R2x. On the other hand, the inclination of the straight line L2 is less than "1" in the range R2y (see FIG. 14). The inclination of the straight line L2 outside the angle changing region R2 is "1" (see FIG. 14).

Figure 14:
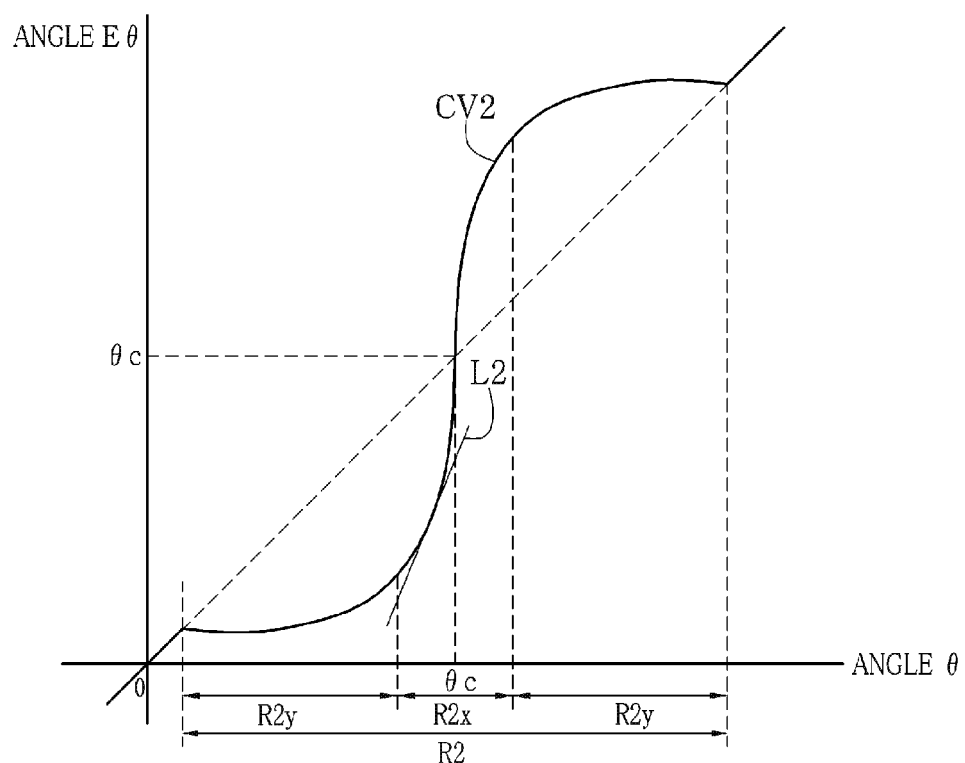
FIG. 14 is graph illustrating a relationship between the angle θ and the angle Eθ that is obtained after the second process (for the signal ratio space)

By the second process (for the signal ratio space), as illustrated in FIG. 14, the angle θ, which is less than the angle θc, of the coordinates (point) in the angle changing region R2 is changed to an angle Eθ which is smaller than the angle θ. The angle θ, which is greater than the angle θc, of the coordinates (point) in the angle changing region R2 is changed to the angle Eθ which is greater than the angle θ. The angle θ outside the angle changing region R2 is changed to the angle Eθ which is identical to the angle θ (identical transformation).

Figure 15:
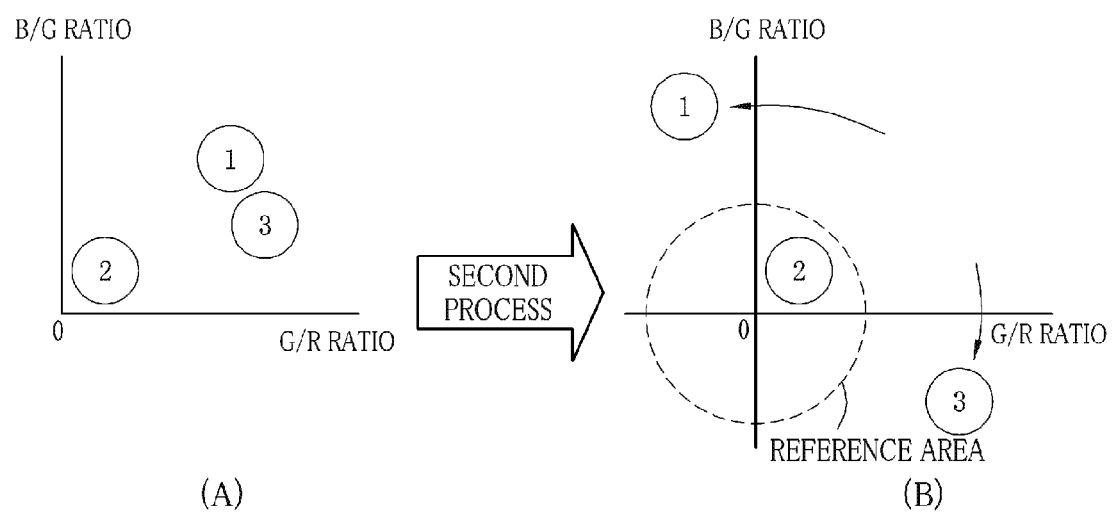
FIG. 15 is an explanatory view illustrating operation and effect of the second process (for the signal ratio space)

Before the second process (for the signal ratio space), as illustrated in the part (A) of FIG. 15, the first observation area and the third observation area are located away from the second observation area, but the first observation area is close to the third observation area. After the second process (for the signal ratio space), as illustrated in the part (B) of FIG. 15, most of the coordinates corresponding to the first observation area are moved to the second quadrant of the signal ratio space and most of the coordinates corresponding to the third observation area are moved to the fourth quadrant of the signal ratio space while the coordinates corresponding to the second observation area are maintained in the reference area. Upon completion of the second process (for the signal ratio space), the Cartesian coordinate conversion process is performed on the radial coordinate r and the angle θ which have been subjected to the second process (for the signal ratio space). Thereby, the second B/G ratio and the second G/R ratio are obtained.

Figure 16:
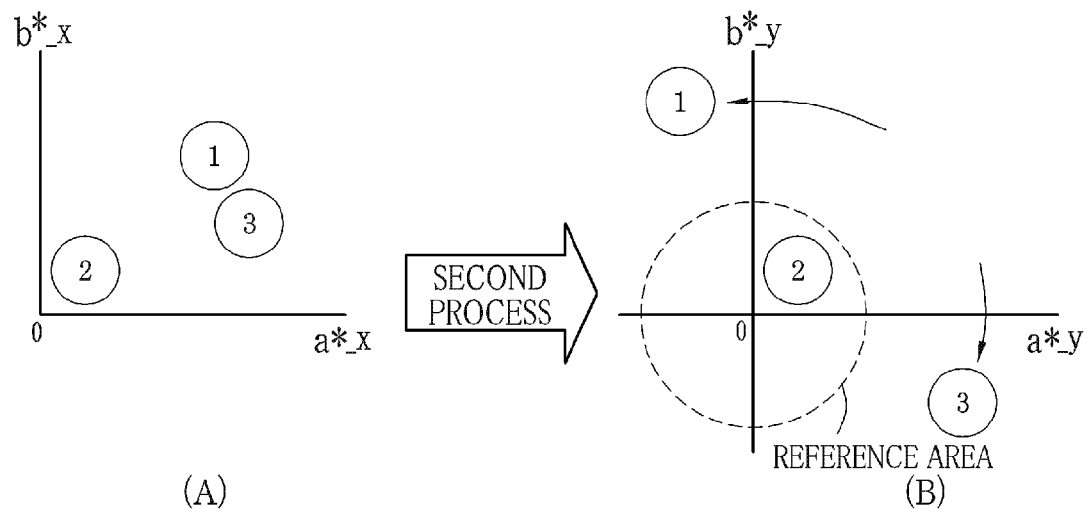
FIG. 16 is an explanatory view illustrating operation and effect of the second process (for the ab space)

Note that in the case where the two or more pieces of first color information are the first components a*_x and b*_x, as illustrated in FIG. 16, a second process (for the ab space) is performed. By the second process, most of the coordinates corresponding to the first observation area are moved to the second quadrant of the second ab space and most of the coordinates corresponding to the third observation area are moved to the fourth quadrant of the second ab space while the coordinates corresponding to the second observation area are maintained in the reference area. Here, the part (A) of FIG. 16 illustrates the distribution of the first to third observation areas before the second process (for the ab space). The part (B) of the FIG. 16 illustrates the distribution of the first to third observation areas after the second process (for the ab space) It is preferred that the brightness adjuster 81 adjusts or corrects the pixel values of the second RGB image signals obtained after the first and second processes (for the ab space). The method for adjusting the pixel values of the second RGB image signals is the same as or similar to the above.

Figure 17:
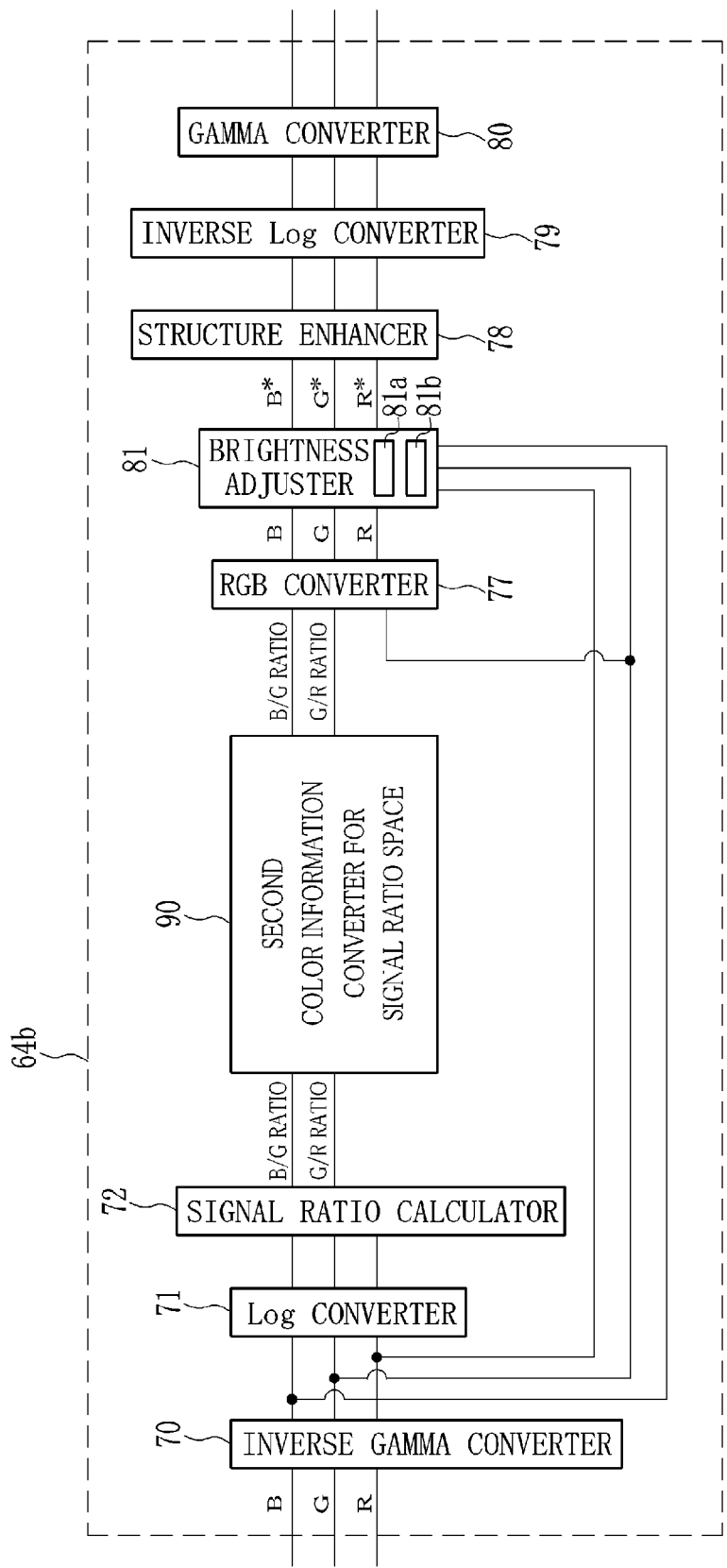
FIG. 17 is a block diagram illustrating functions of a second special image processor.

The second special image processor 64b has the same or similar configuration as that of the first special image processor 64a. However, the second special image processor 64b has a second color information converter 90 (see FIG. 17) (for the signal ratio space) in place of the first color information converter 73 (for the signal ratio space). The second color information converter 90 performs a second color information conversion process (for the signal ratio space) on the first B/G ratio and the first G/R ratio, which are calculated by the signal ratio calculator 72, to convert the first B/G ratio and the first G/R ratio into a second B/G ratio and a second G/R ratio (which correspond to "two or more pieces of second color information" of the present invention)

The second color information converter 90 is composed of a two-dimensional LUT (Look Up Table) in which the first B/G ratio, the first G/R ratio, the second B/G ratio, and the second G/R ratio are stored in association with each other. The second B/G ratio and the second G/R ratio are obtained by the second color information conversion process (for the signal ratio space) based on the first B/G ratio and the first G/R ratio. The second color information conversion process will be detailed below.

Figure 18:
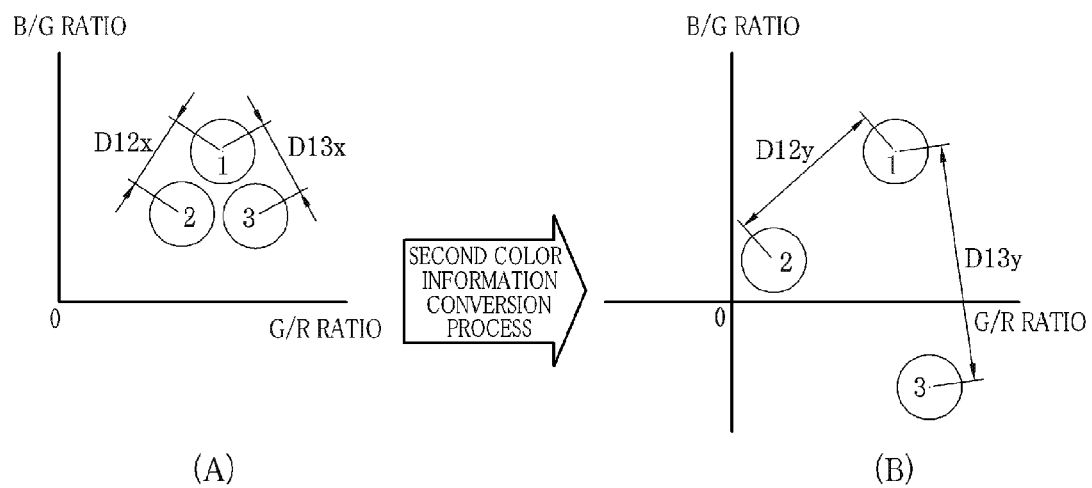
FIG. 18 is an explanatory view illustrating a second color information conversion process (for the signal ratio space)

As illustrated in the part (A) of FIG. 18, the first to third observation areas are distributed in the first signal ratio space formed by the first B/G ratio (the vertical axis) and the first G/R ratio (the horizontal axis). In the first signal ratio space, there is a difference D12$x$ between the first and second observation areas (for example, between the average value of the first observation area and the average value of the second observation area). There is a difference D13$x$ between the first and third observation areas (for example, between the average value of the first observation area and the average value of the third observation area), in a manner similar to the part (A) of FIG. 5.

As illustrated in the part (B) of FIG. 18, the first to third observation areas are distributed in the second signal ratio space formed by the second B/G ratio (the vertical axis) and the second G/R ratio (the horizontal axis), which are obtained by the second color information conversion process (for the signal ratio space). In the second signal ratio space, there is a difference D12$y$ between the first and second observation areas (for example, between the average value of the first observation area and the average value of the second observation area). There is a difference D13$y$ between the first and third observation areas (for example, between the average value of the first observation area and the average value of the third observation area).

The difference D12$y$ represents a difference in saturation between the colors in the first observation area and the colors in the second observation area in the image, in a manner similar to the difference D12$x$. The difference D12$y$ is greater than the difference D12$x$. The difference D13$y$ represents a difference in hue between the colors in the first observation area and the colors in the third observation area in the image, in a manner similar to the difference D13$x$. The difference D13$y$ is greater than the difference D13$x$. Furthermore, the coordinates corresponding to the first observation area in the second signal ratio space are identical to the coordinates corresponding to the first observation area in the first signal ratio space. In other words, the saturation and the hue of the first observation area before the second color information conversion process are identical to those of the first observation area after the second color information conversion process.

As described above, the difference between the first and second observation areas and the difference between the first and third observation areas are increased by the first color information conversion process (for the signal ratio space). The saturation and the hue of the first observation area are maintained unchanged through the second color information conversion process (for the signal ratio space). Thereby, in the second special image produced from the second B/G ratio and the second G/R ratio, which have been subjected to the second color information conversion process (for the signal ratio space), the color of the normal portion displayed is maintained while the color of the atrophic mucosa of the atrophic portion with the atrophic gastritis is displayed in faded colors. In the second special image, the color of the deep blood vessels, which are located beneath the atrophic mucosa and seen through the atrophic mucosa, is changed from red to magenta or the like. Thereby the deep blood vessels are displayed clearly. Thus, the second special image displayed shows actual colors, so that the difference in color between the normal portion and the atrophic portion is clear when a patient has the atrophic gastritis.

Note that, in the case where the two or more pieces of first color information are the first components a*_x and b*_x, the operation and the effect similar to the above are obtained by performing a second color information conversion process (for the ab space) on the first components a*_x and b*_x, in a manner similar to the second color information conversion process (for the signal ratio space) described above.

Figure 19:
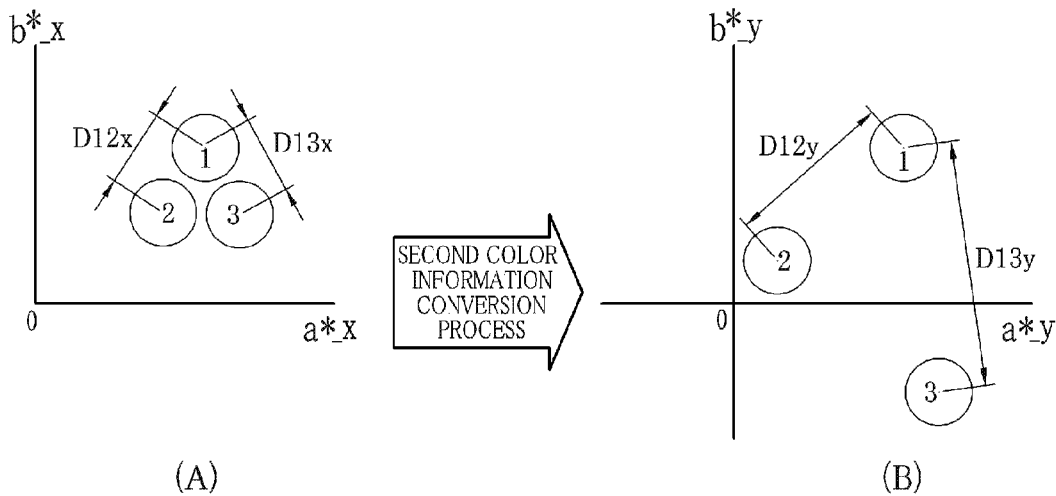
FIG. 19 is an explanatory view illustrating a second color information conversion process (for the ab space)

The part (A) of FIG. 19 illustrates the distribution of the first to third observation areas, the difference D12$x$ between the first and second observation areas, and the difference D13$x$ between the first and third observation areas in the first ab space formed by the first components a*_x and b*_x. The part (B) of FIG. 19 illustrates the distribution of the first to third observation areas, the difference D12$y$ between the first and second observation areas, and the difference D13$y$ between the first and third observation areas in the second ab space formed by the second components a*_y and b*_y, which are obtained by the second color information conversion process (for the ab space). As illustrated in FIG. 19, the second color information conversion process (for the ab space) increases the difference between the first and second observation areas and the difference between the first and third observation areas while the coordinates corresponding to the first observation area are maintained unchanged.

The second color information conversion process (for the signal ratio space) is composed of the polar coordinate conversion process, the first process and a third process (for the signal ratio space), and the Cartesian coordinate conversion process. The polar coordinate conversion process, the first process (for the signal ratio space), and the Cartesian coordinate conversion process are the same as or similar to the above and descriptions thereof are omitted.

Figure 20:
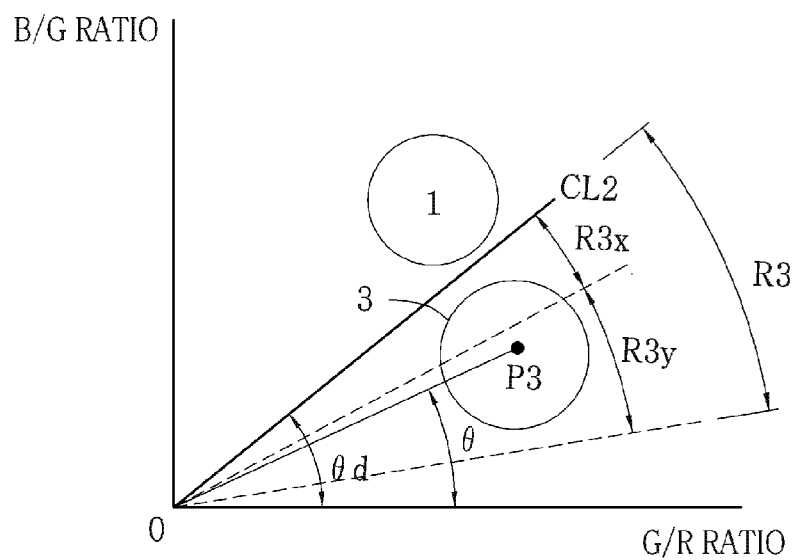
FIG. 20 is an explanatory view illustrating a third process for the signal ratio space.

In the third process (for the signal ratio space), the angle θ of the coordinates corresponding to the third observation area is changed based on the radial coordinate r and the angle θ which are obtained after the first process (for the signal ratio space), to move the coordinates which correspond to the third observation area while the coordinates which correspond to the first observation area are maintained unchanged. In the third process (for the signal ratio space) illustrated in FIG. 20, the angle θ of coordinates (point) P3 within the angle changing region R3 is changed while the angle θ of coordinates outside the angle changing region R3 is not changed. The angle changing region R3 is set to include the third observation area and exclude the first observation area. Note that in the third process (for the signal ratio space), the radial coordinate r of the coordinates in the angle changing region R3 is not changed.

Figure 21:
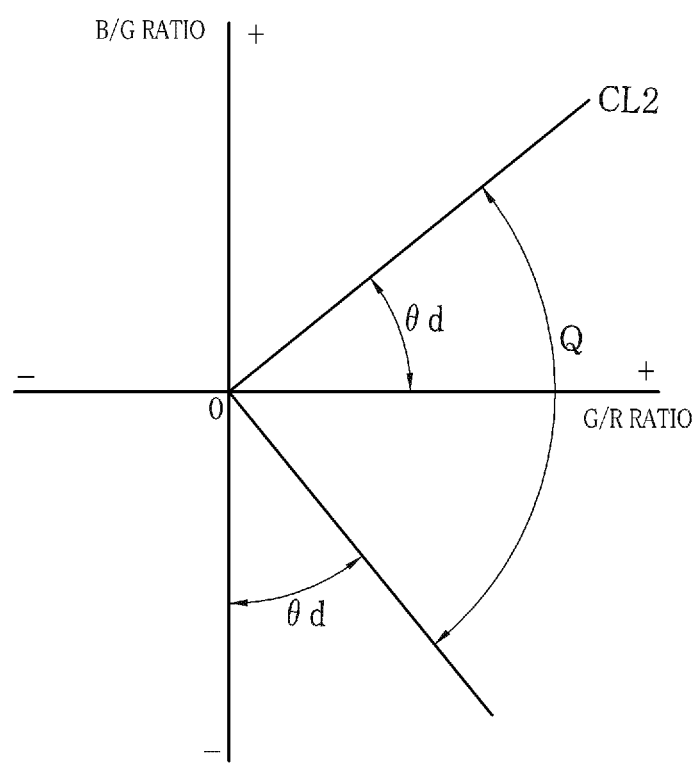
FIG. 21 is a graph illustrating a region within which the coordinates having the angle θ in an angle changing region R3 are to be moved.

A second center line CL2 is set between the first observation area and the third observation area in the angle changing region R3. The second center line CL2 is set at an angle θd. The coordinates having the angle θ which is less than or equal to the angle θd in the angle changing region R3 are rotated in the clockwise direction. Note that, with regard to the angle which is within a range R3$x$ extending from the second center line CL2, it is preferred to perform the expansion process for changing the angle θ at an angle change rate Wx, which is greater than "1". With regard to the angle θ which is within a range R3$y$ outside the range R3$x$, it is preferred to perform the compression process for changing the angle θ at an angle change rate Wy, which is less than "1". It is preferred to move the coordinates, which are located in the angle changing region R3, within a region extending −90° (degrees) from the second center line CL2 (e.g. a region Q extending from "270°+θd" to "θd" in the case where the "positive" horizontal axis is 0° and an angle is expressed in degree from 0° to 360° in the signal ratio space (see FIG. 21)) through the third process (for the signal ratio space). Note that in a case where the angle change rate is "1", the angle θ does not change when subjected to the process for changing the angle θ.

Here, an angle change rate is represented by the inclination of a straight line "L3", being the tangent line of a curve CV3. The curve CV3 depicts the relationship between angles θ and Eθ. The inclination of the straight line L3 is greater than "1" in the range R3x. On the other hand, the inclination of the straight line L3 is less than "1" in the range R3y (see FIG. 22). The inclination of the straight line L3 outside the angle changing region R3 is "1" (see FIG. 22).

Figure 22:
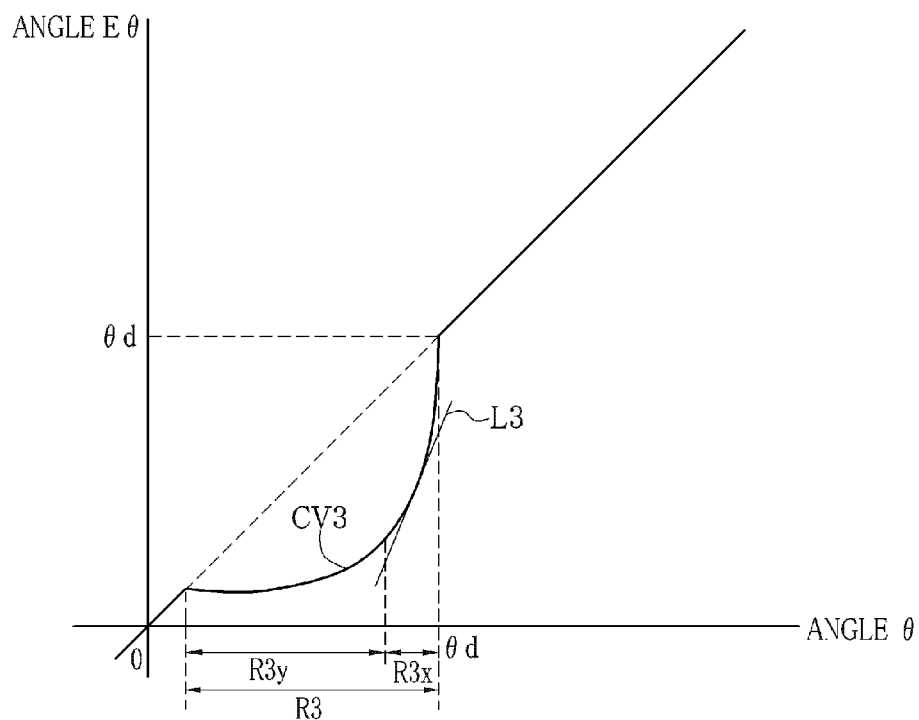
FIG. 22 is a graph illustrating a relationship between the angle θ and the angle Eθ obtained after the third process (for the signal ratio space)

By the third process (for the signal ratio space), as illustrated in FIG. 22, the angle θ which is located in the angle changing region R3 is changed to the angle Eθ which is smaller than the angle θ. The angle θ outside the angle changing region R3 is changed to the angle Eθ which is identical to the angle θ (identical transformation).

Figure 23:
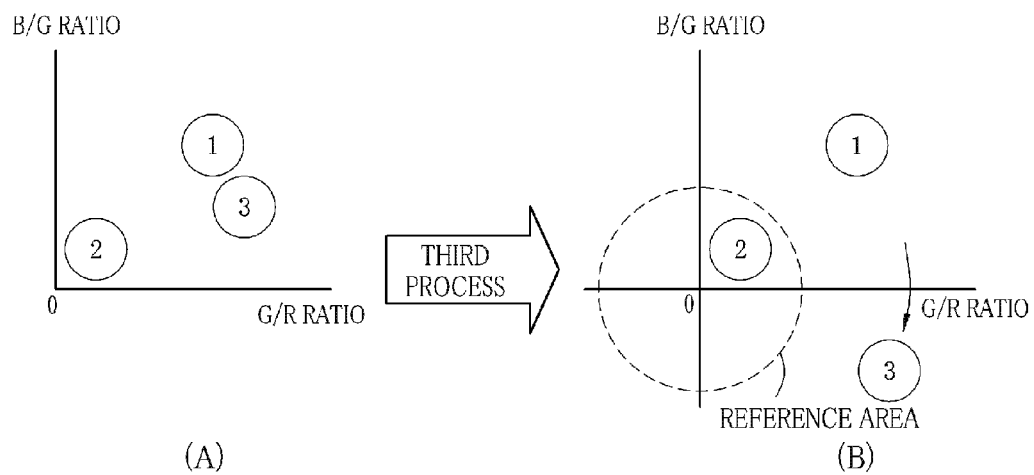
FIG. 23 is an explanatory view illustrating operation and effect of the third process (for the signal ratio space)

Before the third process (for the signal ratio space), as illustrated in the part (A) of FIG. 23, the first observation area (denoted as "1" in FIG. 23) and the third observation area (denoted as "3" in FIG. 23) are located away from the second observation area (denoted as "2" in FIG. 23), but the first observation area is close to the third observation area. After the third process (for the signal ratio space), as illustrated in the part (B) of FIG. 23, most of the coordinates corresponding to the third observation area are moved to the fourth quadrant of the signal ratio space while the coordinates corresponding to the second observation area are maintained in the reference area and while the coordinates corresponding to the first observation area are maintained unchanged. Moving the coordinates which correspond to the third observation area from the first quadrant to the fourth quadrant means changing the hue while the saturation is maintained in the second special image. Thereby the coordinates corresponding to the first observation area, the coordinates corresponding to the second observation area, and the coordinates corresponding to the third observation area are moved away from each other.

Figure 24:
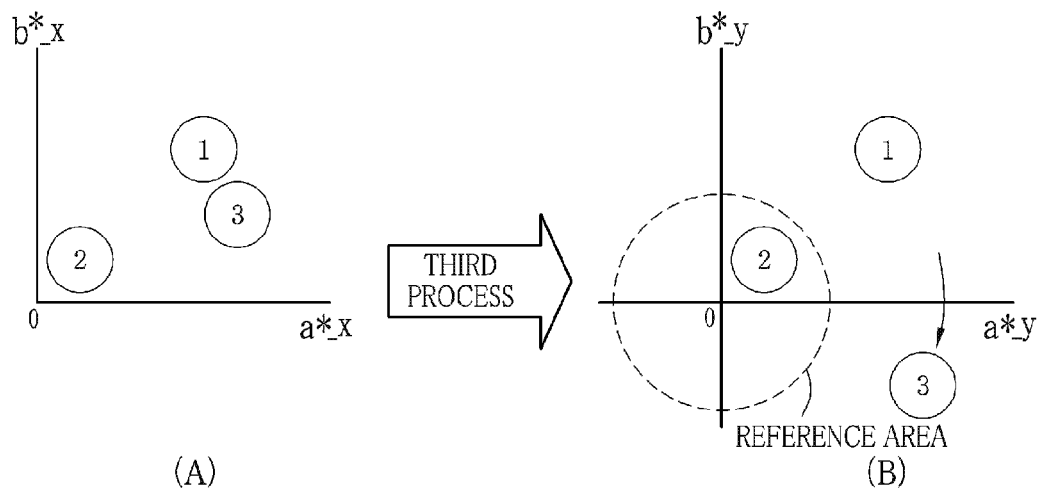
FIG. 24 is an explanatory view illustrating operation and effect of the third process (for the ab space)

Note that, in the case where the two or more pieces of first color information are the first components a*_x and b*_x as illustrated in FIG. 24, most of the coordinates corresponding to the third observation area are moved to the fourth quadrant of the ab space by the third process (for the ab space) while the coordinates corresponding to the second observation area are maintained in the reference area and while the coordinates corresponding to the first observation area are maintained unchanged. Here, the part (A) of FIG. 24 illustrates the distribution of the first to third observation areas before the third process (for the ab space). The part (B) of FIG. 24 illustrates the distribution of the first to third observation areas after the third process (for the ab space). It is preferred that the brightness adjuster 81 adjusts the pixel values of the second RGB image signals obtained after the first and third processes (for the ab space). The method for adjusting the pixel values of the second RGB image signals is the same as or similar to that described above.

Figure 25:
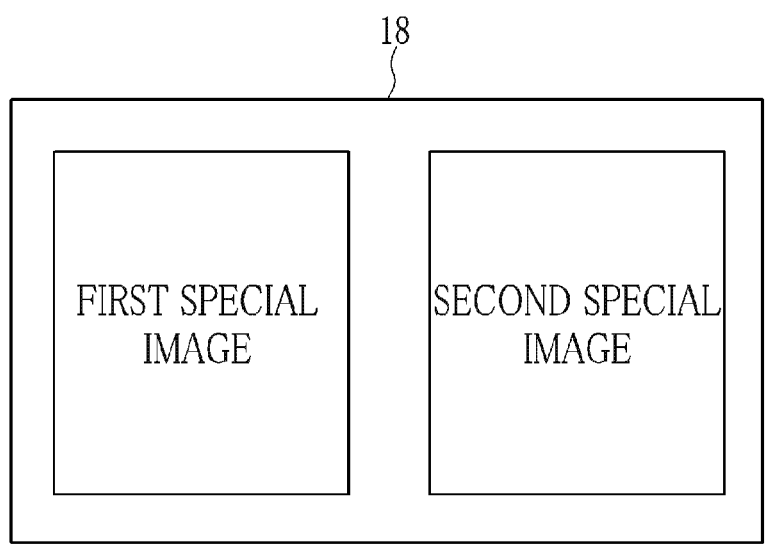
FIG. 25 is an image view of a monitor displaying the first special image and the second special image at a time.

Based on the first special image produced by the first special image processor 64a and the second special image produced by the second special image processor 64b, the simultaneous display image processor 64c produces a special image for simultaneous display. As illustrated in FIG. 25, the monitor 18 displays the first special image on one side and the second special image on the other side, based on the special image for simultaneous display. In the first special image, a boundary between the normal portion and the atrophic portion is clear enough to facilitate finding the position of the atrophic portion or the like. However, the normal portion is displayed in pseudo color, which is not the actual color of the gastric mucosa. The pseudo color gives a doctor an unnatural impression. In the second special image, on the other hand, the boundary between the normal portion and the atrophic portion is clear to some extent as compared with that in the first special image, but the color of the normal portion is displayed in actual color of the stomach, so that the second special image gives a doctor a natural impression. The simultaneous display of the first and second special images allows a doctor to detect the boundary between the normal portion and the atrophic portion while checking the color of the normal portion.

Figure 26:
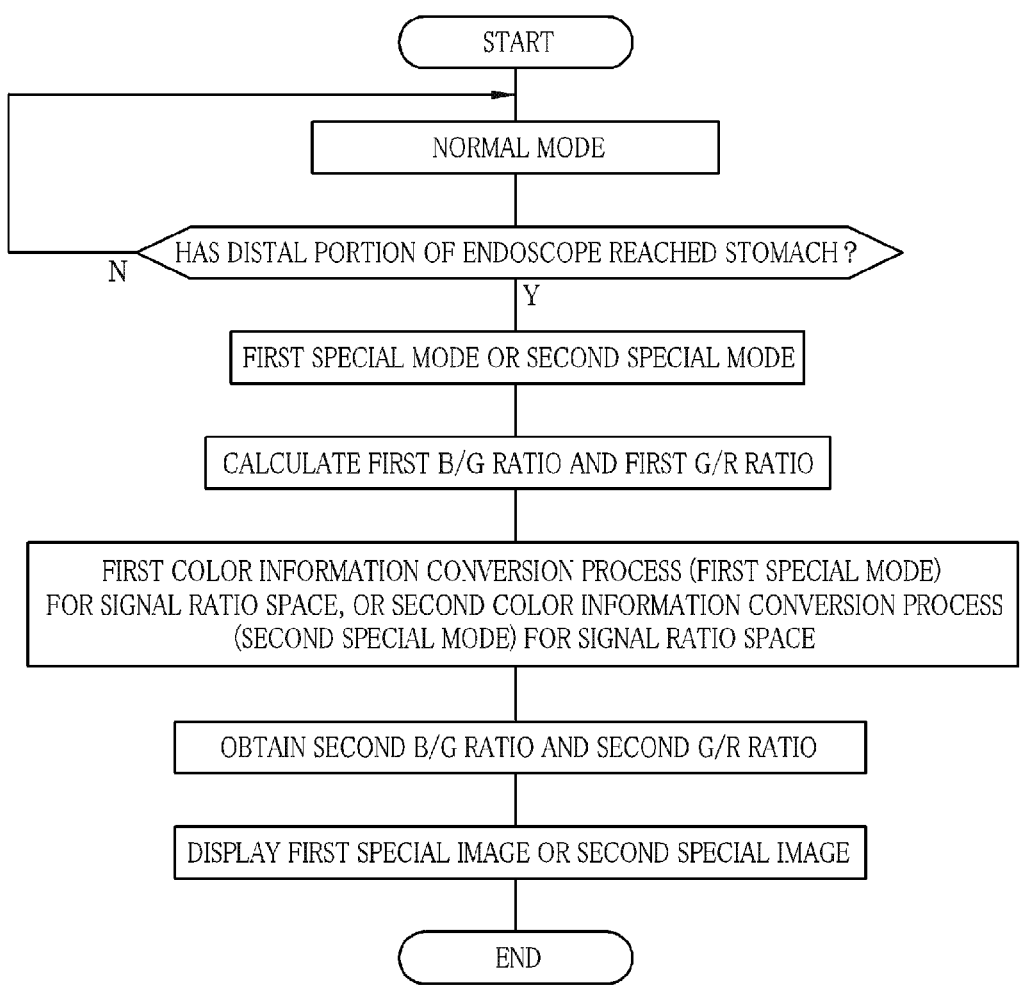
FIG. 26 is a flowchart illustrating steps of an embodiment of the present invention.

Hereinafter, referring to a flowchart illustrated in FIG. 26, an operation of the present invention is described. First, the mode is set to the normal mode. The insertion section 12a of the endoscope 12 is inserted into the body cavity. After the distal portion 12d of the insertion section 12a reached the stomach, the mode SW 13a is operated to switch from the normal mode to the first or second special mode. Note that the mode is switched to the simultaneous display mode in the case where a doctor performs a diagnosis of the atrophic gastritis while observing both of the first and second special images.

Based on the RGB image signals obtained after the mode is switched to the first or second special mode, the signal ratio calculator 72 calculates the first B/G ratio and the first G/R ratio. Then, in the case of the first special mode, the first color information converter 73 (for the signal ratio space) converts the first B/G ratio and the first G/R ratio into the second B/G ratio and the second G/R ratio through the first color information conversion process (for the signal ratio space). The first special image is produced based on the second B/G ratio and the second G/R ratio, which have been subjected to the first color information conversion process. The first special image is displayed on the monitor 18.

In the case of the second special mode, the second color information converter 90 (for the signal ratio space, see FIG. 17) converts the first B/G ratio and the first G/R ratio into the second B/G ratio and the second G/R ratio through the second color information conversion process (for the signal ratio space). The second special image is produced based on the second B/G ratio and the second G/R ratio, which have been subjected to the second color information conversion process (for the signal ratio space). The second special image is displayed on the monitor 18.

Note that the simultaneous display in the simultaneous display mode is not limited to that of the first and second special images. For example, the first or second special image and the normal image may be displayed simultaneously or at a time. In this case, the display images (the normal image and the special image) are produced by the normal image processor unit 62 and the special image processor unit 64, respectively, and then transmitted through the video signal generator 66 to the monitor 18 and displayed thereon.

In the simultaneous display mode, the first special image and a third special image may be displayed simultaneously or at a time. The third special image is produced without being subjected to any of the first and second color information conversion processes. The third special image is produced by a third special image processor (not shown) provided in the special image processor unit 64. Unlike the first and second special image processors 64a and 64b, the third special image processor is not provided with the first and second color information converters, which are necessary for the first and second color information conversion processes (for the signal ratio space). Other than those, the components of the third special image processor are the same as or similar to those of the first and second special image processors 64a and 64b. Note that, in taking the third special image, it is preferred that light in which the light intensity of the violet light V is greater than those of the blue light B, the green light G, and the red light R is emitted. In the third special image taken under the light of such emission conditions, the surface blood vessels are enhanced while the excellent brightness of the entire image is maintained.

In the above embodiment, the signal ratio calculator 72 calculates the first B/G ratio and the first G/R ratio based on the first RGB image signals. Then the first B/G ratio and the first G/R ratio are converted into the second B/G ratio and the second G/R ratio through the first or second color information conversion process (for the signal ratio space). Note that two or more pieces of first color information which differ from the first B/G ratio and the first G/R ratio may be obtained from the first RGB image signals. These two or more pieces of first color information may be converted into two or more pieces of second color information through first or second color information conversion process for a specific feature space.

Figure 27:
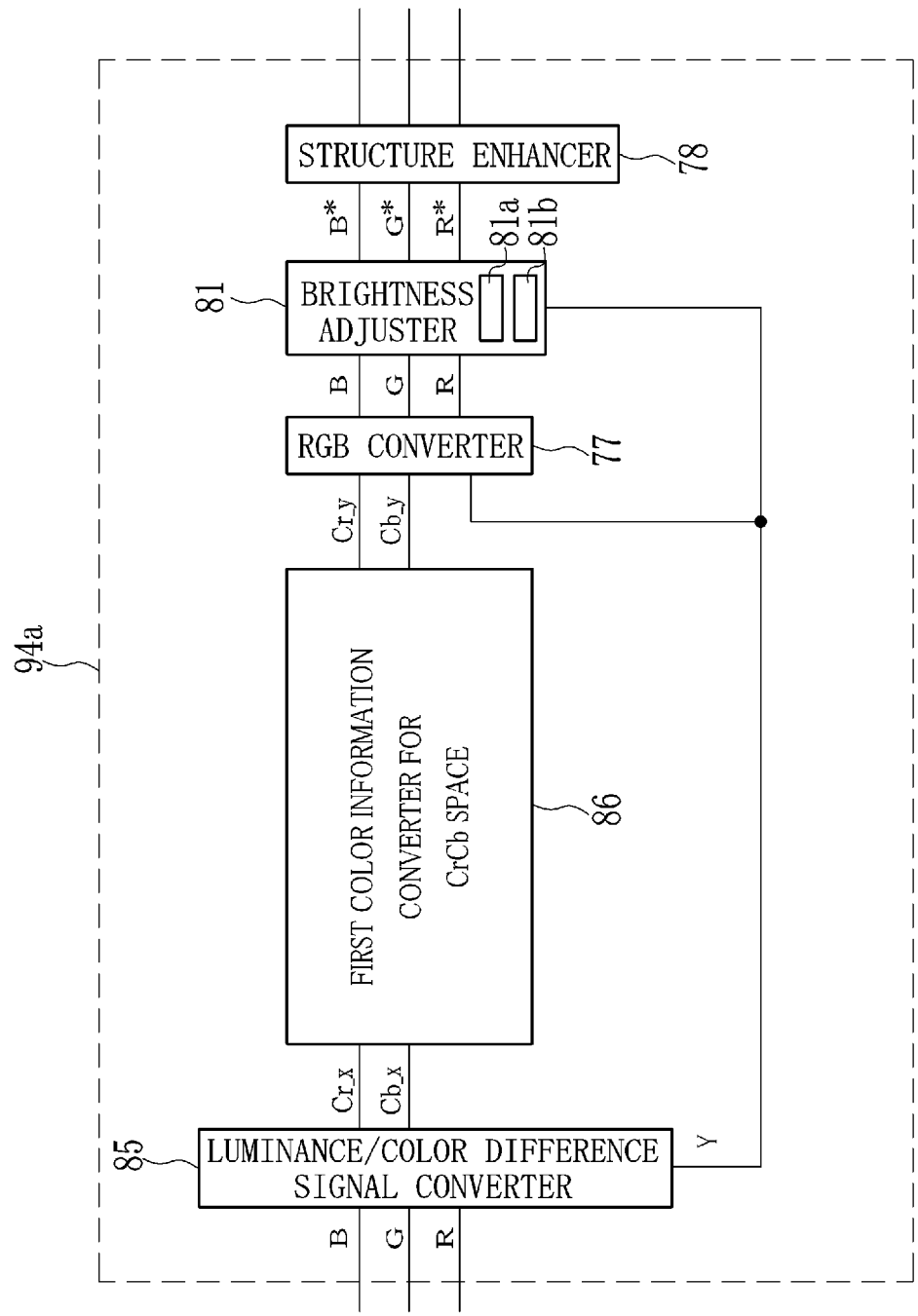
FIG. 27 is a block diagram illustrating functions of the first special image processor having a first color information converter (for a CrCb space)

For example, color difference signals Cr and Cb may be obtained as the two or more pieces of first color information. The first and second color information conversion processes (for a CrCb space) may be performed on the color difference signals Cr and Cb. A first special image processor 94a illustrated in FIG. 27 performs the first color information conversion process (for the CrCb space). Unlike the first special image processor 64a, the first special image processor 94a is not provided with the inverse gamma converter 70, the log converter 71, the signal ratio calculator 72, the first color information converter 73 (for the signal ratio space), the inverse log converter 79, and the gamma converter 80. Instead, the first special image processor 94a comprises a luminance/color difference signal converter 85 and a first color information converter 86 (for the CrCb space). Other than those described above, the components of the first special image processor 94a are the same as or similar to the components of the first special image processor 64a.

The luminance/color difference signal converter 85, which corresponds to the "color information obtaining section" of the present invention, converts the first RGB image signals into the luminance signal Y and first color difference signals Cr_x and Cb_x. A well-known conversion equation is used for the conversion into the first color difference signals Cr_x and Cb_x. The first color difference signals Cr_x and Cb_x are transmitted to the first color information converter 86 (for the CrCb space). The luminance signal Y is transmitted to the RGB converter 77 and the brightness adjuster 81. The RGB converter 77 converts second color difference signals Cr_y and Cb_y, which have been subjected to the first color information conversion process, and the luminance signal Y into the second RGB image signals. The brightness adjuster 81 adjusts or corrects the pixel values of the second RGB image signals with the use of the luminance signal Y (the first brightness information Yin) and the second brightness information (the second brightness information Yout), which is calculated by the second brightness information calculator 81b. Note that the method for calculating the second brightness information Yout and the method for adjusting the pixel values of the second RGB image signals are the same as or similar to those of the first special image processor 64a.

The first color information converter 86 (for the CrCb space) performs the first color information conversion process (for the CrCb space) on the first color difference signals Cr_x and Cb_x to convert the first color difference signals Cr_x and Cb_x into the second color difference signals Cr_y and Cb_y. The first color information converter 86 is composed of a two-dimensional LUT (Look Up Table), in which the first color difference signals Cr_x and Cb_x and the second color difference signals Cr_y and Cb_y are stored in association with each other. The second color difference signals Cr_y and Cb_y are obtained by the first color information conversion process (for the CrCb space) based on the first color difference signals Cr_x and Cb_x. The first color information conversion process (for the CrCb space) will be detailed below.

Figure 28:
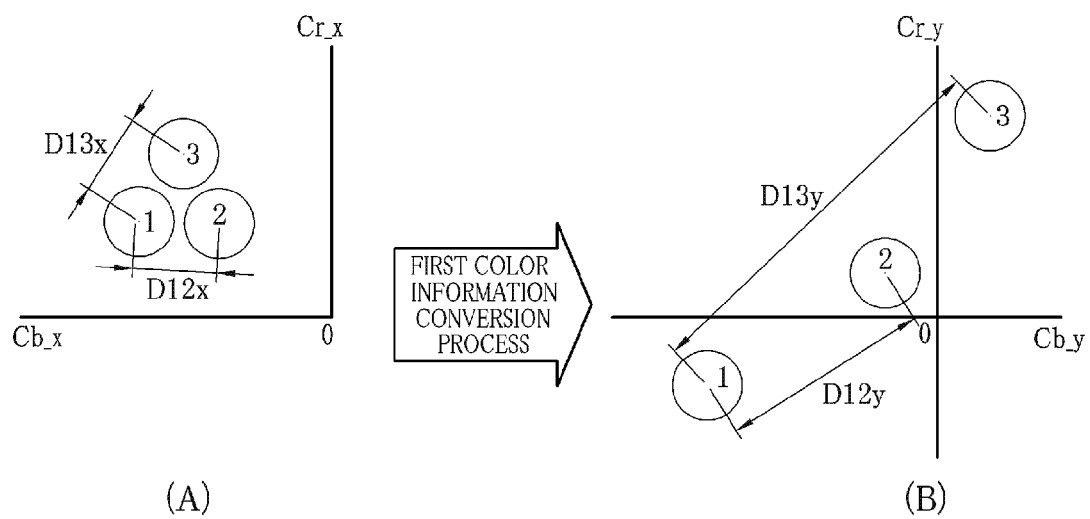
FIG. 28 is an explanatory view illustrating the first color information conversion process (for the CrCb space)

As illustrated in the part (A) of FIG. 28, the first observation area, the second observation area, and the third observation area are distributed in the second quadrant of the first CrCb space (which corresponds to the "first feature space" of the present invention) formed by the first color difference signals Cr_x and Cb_x. In the first CrCb space, there is a difference D12$x$ between the first and second observation areas (for example, between the average value of the first observation area and the average value of the second observation area). There is a difference D13$x$ between the first and third observation areas (for example, between the average value of the first observation area and the average value of the third observation area). The difference D12$x$ represents a difference in saturation between colors in the first observation area and colors in the second observation area in the image. The difference D13$x$ represents a difference in hue between the colors in the first observation area and colors in the third observation area in the image.

As illustrated in the part (B) of FIG. 28, the first, second, and third observation areas are in the different quadrants, respectively, in the second CrCb space formed by the second color difference signals Cr_y and Cb_y, which are obtained by the first color information conversion process (for the CrCb space). In the second CrCb space (which corresponds to the "second feature space" of the present invention), there is a difference D12$y$ between the first and second observation areas (for example, between the average value of the first observation area and the average value of the second observation area). There is a difference D13$y$ between the first and third observation areas (for example, between the average value of the first observation area and the average value of the third observation area).

The difference D12$y$ represents differences in saturation and hue between the colors in the first observation area and the colors in the second observation area in the image. The difference D12$y$ is greater than the difference D12$x$. The difference D13$y$ represents a difference in hue between the colors in the first observation area and the colors in the third observation area in the image. The difference D13$y$ is greater than the difference D13$x$. Furthermore, the coordinates corresponding to the first observation area in the second CrCb space differ from the coordinates corresponding to the first observation area in the first CrCb space. In other words, at least one of the saturation and the hue of the first observation area after the first color information conversion process (for the CrCb space) differs from that before the first color information conversion process.

As described above, the first color information conversion process (for the CrCb space) increases the difference between the first and second observation areas and the difference between the first and third observation areas and changes at least one of the saturation and the hue of the first observation area. The first special image is produced in a like manner, from the second color difference signals Cr_y and Cb_y, which have been subjected to the first color information conversion process (for the CrCb space).

Figure 29:
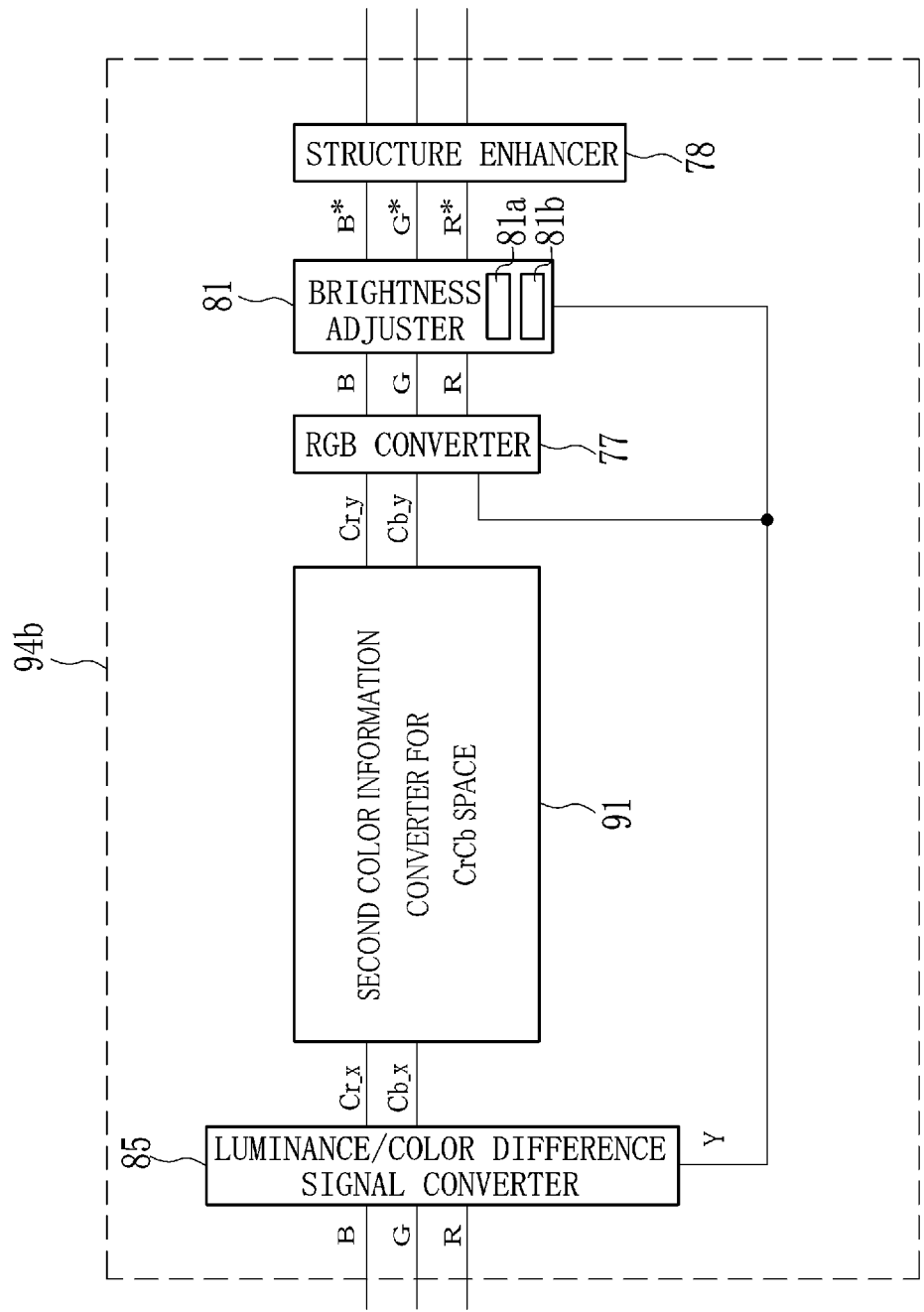
FIG. 29 is a block diagram illustrating functions of the second special image processor having a second color information converter (for the CrCb space)

A second special image processor 94b (see FIG. 29), which has similar or substantially the same configuration as that of the first special image processor 94a, performs the second color information conversion process (for the CrCb space). The second special image processor 94b is similar to or the same as the first special image processor 94a except that the second special image processor 94b has a second color information converter 91 (for the CrCb space) in place of the first color information converter 86 (for the CrCb space).

The second color information converter 91 (for the CrCb space) performs the second color information conversion process (for the CrCb space) on the first color difference signals Cr_x and Cb_x to convert the first color difference signals Cr_x and Cb_x into the second color difference signals Cr_y and Cb_y. The second color information converter 91 (for the CrCb space) is composed of a two-dimensional LUT (Look Up Table), in which the first color difference signals Cr_x and Cb_x and the second color difference signals Cr_y and Cb_y, which are obtained by the second color information conversion process (for the CrCb space) based on the first color difference signals Cr_x and Cb_x, are stored in association with each other. The second color information conversion process (for the CrCb space) will be detailed below.

Figure 30:
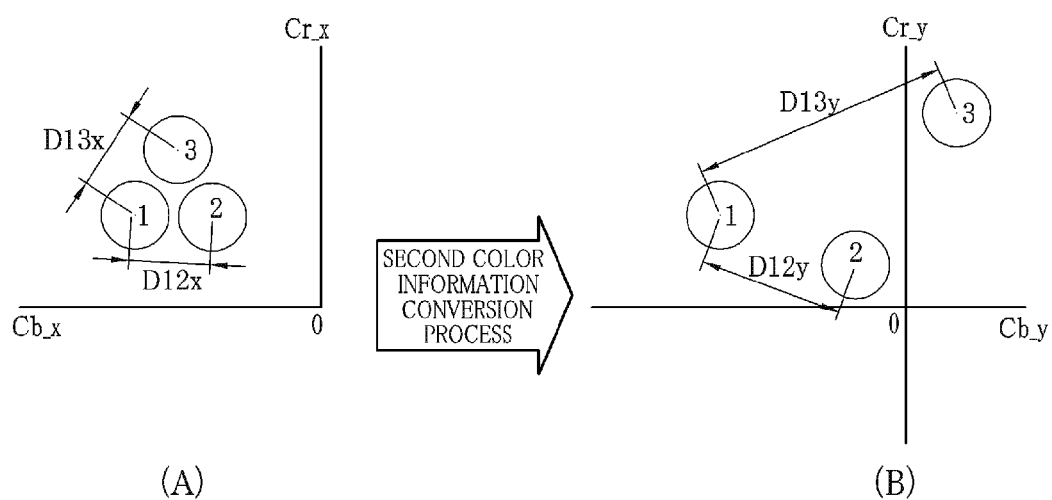
FIG. 30 is an explanatory view illustrating the second color information conversion process (for the CrCb space)

As illustrated in the part (A) of FIG. 30, the first, second, and third observation areas are in the second quadrant in the first CrCb space formed by the first color difference signals Cr_x and Cb_x and there is the difference D12x (the difference in saturation) between the first and second observation areas and there is the difference D13x (the difference in hue) between the first and third observation areas, as with the case illustrated in the part (A) of FIG. 28. As illustrated in the part (B) of FIG. 30, the first and second observation areas are in the second quadrant but the third observation area is in the first quadrant in the second CrCb space formed by the second color difference signals Cr_y and Cb_y, which are obtained by the second color information conversion process (for the CrCb space). In the second CrCb space, there is a difference D12y between the first and second observation areas. There is a difference D13y between the first and third observation areas.

The difference D12y represents a difference in saturation between the colors in the first observation area and the colors in the second observation area in the image. The difference D12y is greater than the difference D12x. The difference D13y represents a difference in hue between the colors in the first observation area and the colors in the third observation area in the image. The difference D13y is greater than the difference D13x. Furthermore, the coordinates corresponding to the first observation area in the second CrCb space are identical to the coordinates corresponding to the first observation area in the first CrCb space. In other words, the saturation and the hue of the first observation area are unchanged by the second color information conversion process (for the CrCb space).

As described above, the second color information conversion process (for the CrCb space) increases the difference between the first and second observation areas and the difference between the first and third observation areas while the saturation and the hue of the first observation area are maintained unchanged. The second special image is produced from the second color difference signals Cr_y and Cb_y, which have been subjected to the second color information conversion process (for the CrCb space), in a manner similar to the above.

Figure 31:
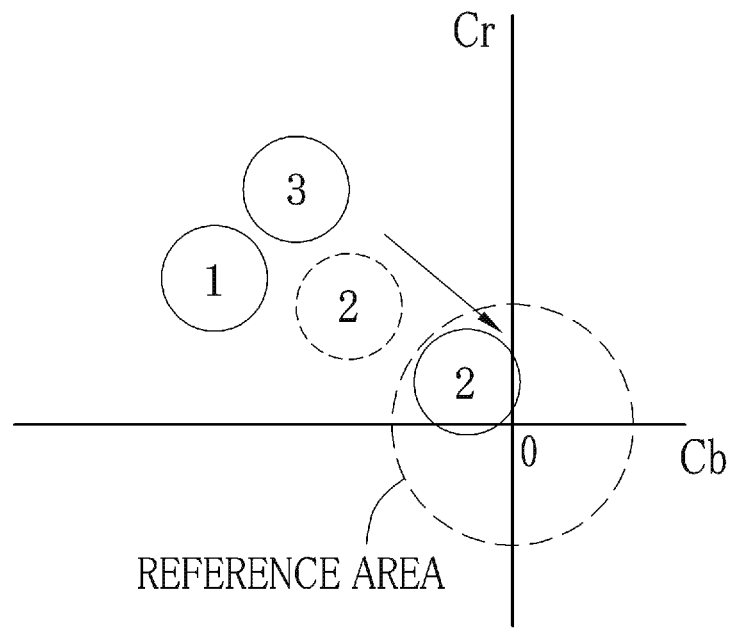
FIG. 31 is an explanatory view illustrating the first process (for the CrCb space)

The first color information conversion process (for the CrCb space) is composed of a polar coordinate conversion process, first and second processes (for the CrCb space), and a Cartesian coordinate conversion process. First, the first color difference signals Cr_x and Cb_x are converted into a radial coordinate r and an angle $\theta$ through the polar coordinate conversion process. Then, as illustrated in FIG. 31, the radial coordinate of the coordinates corresponding to the second observation area is changed by the first process (for the CrCb space) to move the coordinates which correspond to the second observation area to the reference area that contains the origin point of the CrCb space. The reference area refers to a region with low saturation, excluding the first and third observation areas which have been subjected to the first process (for the Cb-Cr space). In the first process (for the Cb-Cr space), the coordinates corresponding to the first and third observation areas are maintained unchanged. Here, the method for moving the coordinates of each observation area is similar to that used for the first process (for the signal ratio space).

Figure 32:
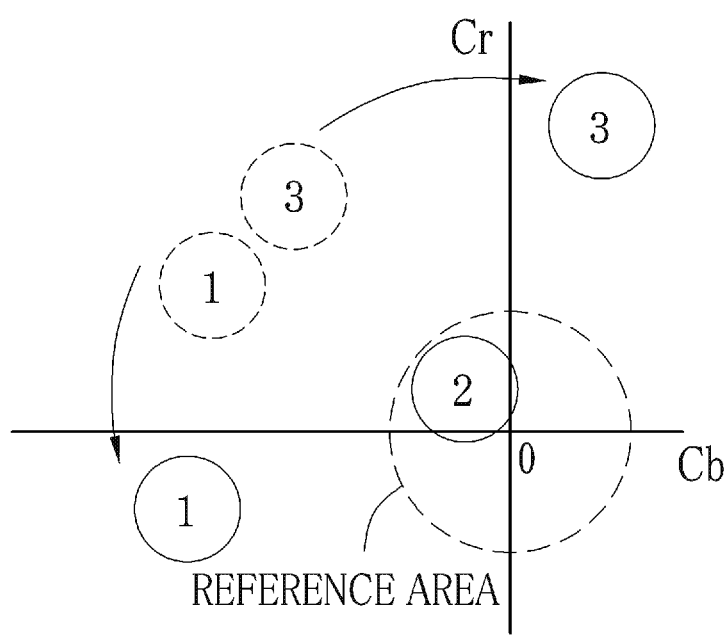
FIG. 32 is an explanatory view illustrating the second process (for the CrCb space)

In the second process (for the CrCb space) illustrated in FIG. 32, the coordinates corresponding to the first observation area and the coordinates corresponding to the third observation area are moved away from each other while the coordinates corresponding to the second observation area are maintained in the reference area. The method for moving the coordinates which correspond to the first observation area and the coordinates which correspond to the third observation area is similar to that used for the second process (for the signal ratio space), namely, the angle S of the coordinates is expanded or compressed. The radial coordinate r and the angle $\theta$ which are obtained after the second process (for the CrCb space) are converted into the second color difference signals Cr_y and Cb_y through the Cartesian coordinate conversion process.

The second color information conversion process (for the CrCb space) is composed of a polar coordinate conversion process, first and third processes (for the CrCb space), and a Cartesian coordinate conversion process. The polar coordinate conversion process, the first process (for the CrCb space), and the Cartesian coordinate conversion process are similar to those of the first color information conversion process (for the CrCb space).

Figure 33:
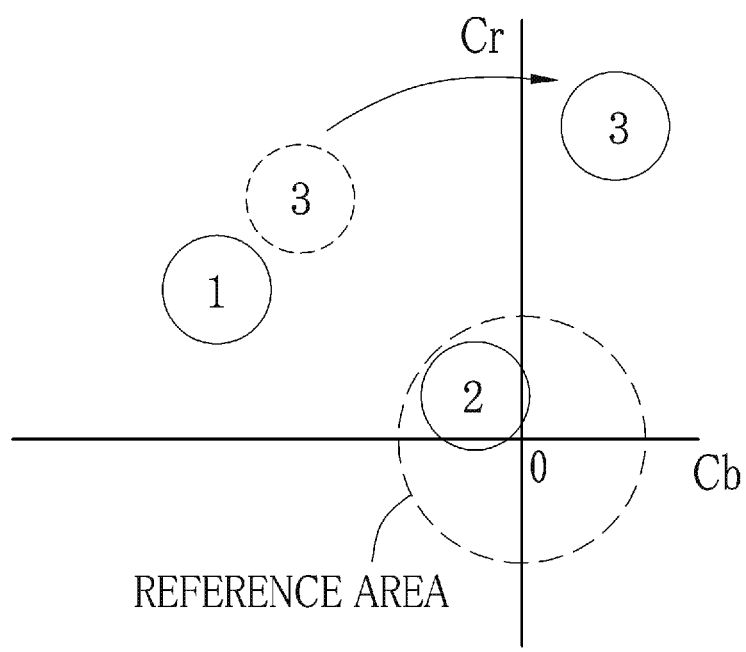
FIG. 33 is an explanatory view illustrating the third process (for the CrCb space)

In the third process (for the CrCb space), as illustrated in FIG. 33, only the coordinates corresponding to the third observation area are moved so as to be away from the first observation area while the coordinates corresponding to the second observation area are maintained in the reference area and while the coordinates corresponding to the first observation area are maintained unchanged. The method for moving the coordinates which correspond to the third observation area is similar to that used in the third process (for the signal ratio space), namely, the angle $\theta$ is expanded or compressed.

Figure 34:
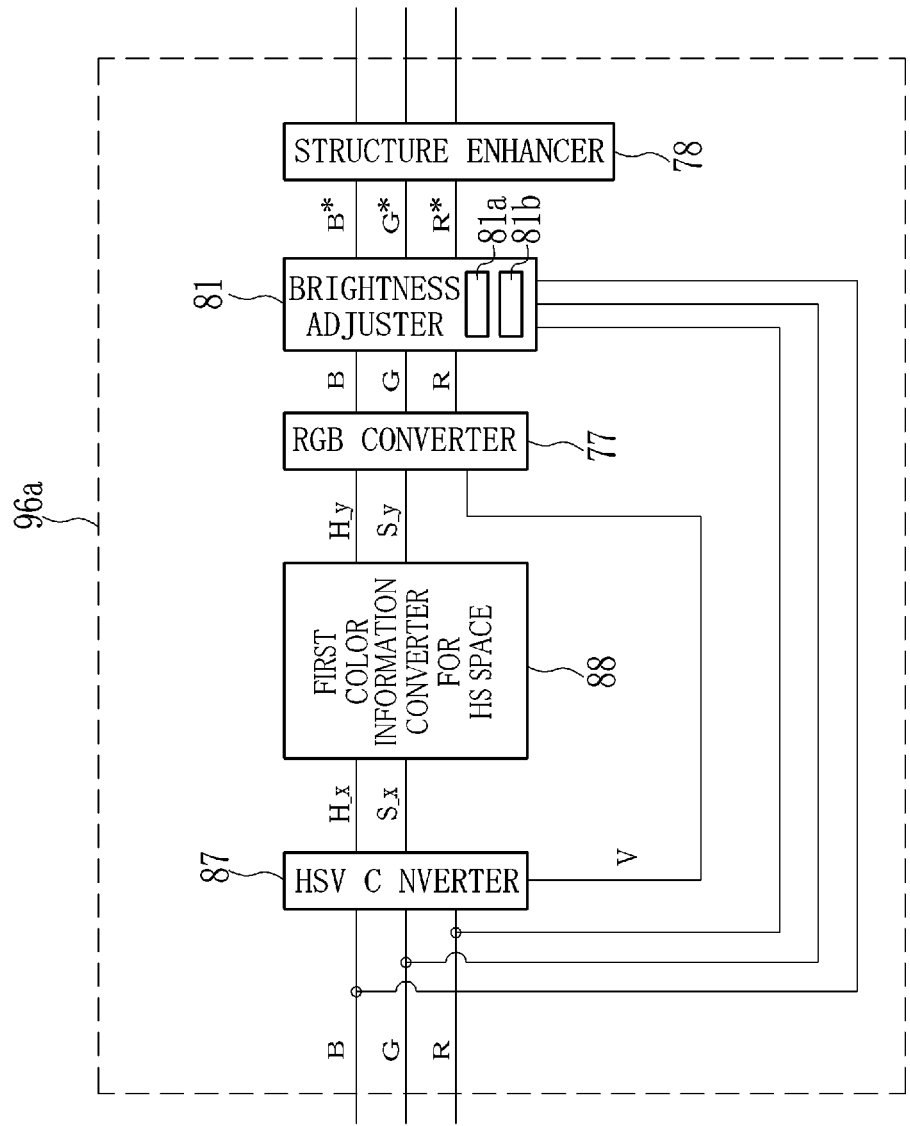
FIG. 34 is a block diagram illustrating functions of a first special image processor having a first color information converter (for a HS space)

The color information may be hue H and saturation S. The first and second color information conversion processes (for the HS space) may be performed on the hue H and the saturation S. A first special image processor 96a (see FIG. 34) performs the first color information conversion process (for the HS space). Unlike the first special image processor 64a, the first special image processor 96a is not provided with the inverse gamma converter 70, the Log converter 71, the signal ratio calculator 72, the first color information converter 73 (for the signal ratio space), the inverse Log converter 79, and the gamma converter 80. Instead, the first special image processor 96a comprises an HSV converter 87 and a first color information converter 88 (for the HS space). Other than those, the first special image processor 96a is the same as or similar to the first special image processor 64a.

The HSV converter 87, which corresponds to the "color information obtaining section" of the present invention, converts the first RGB image signals into first hue H_x, first saturation S_x, and value (lightness or brightness) V. Well-known conversion equations are used for the conversion into the first hue H_x, the first saturation S_x, and the value V. The first hue H_x and the first saturation S_x are transmitted to the first color information converter 88 (for the HS space). The value V is transmitted to the RGB converter 77. The RGB converter 77 converts second hue H_y and second saturation S_y, which have been subjected to the first color information conversion process (for the HS space), and the value V into the second RGB image signals. The brightness adjuster 81 adjusts the pixel values of the second RGB image signals with the use of the first brightness information Yin calculated by the first brightness information calculator 81a and the second brightness information Yout calculated by the second brightness information calculator 81b. Note that the methods for calculating the first brightness information Yin and the second brightness information Yout and the method for adjusting the pixel values of the second RGB image signals are the same as or similar to those of the first special image processor 64a.

The first color information converter 88 (for the HS space) performs the first color information conversion process (for the HS space) on the first hue H_x and the first saturation S_x to convert the first hue H_x and the first saturation S_x into the second hue H_y and the second saturation S_y. The first color information converter 88 (for the HS space) is composed of a two-dimensional LUT (Look Up Table), in which the first hue H_x, the first saturation S_x, the second hue H_y, and the second saturation S_y are stored in association with each other. The second hue H_y and the second saturation S_y are obtained by the first color information conversion process (for the HS space) that is performed based on the first hue H_x and the first saturation S_x. The first color information conversion process (for the HS space) will be detailed below.

Figure 35:
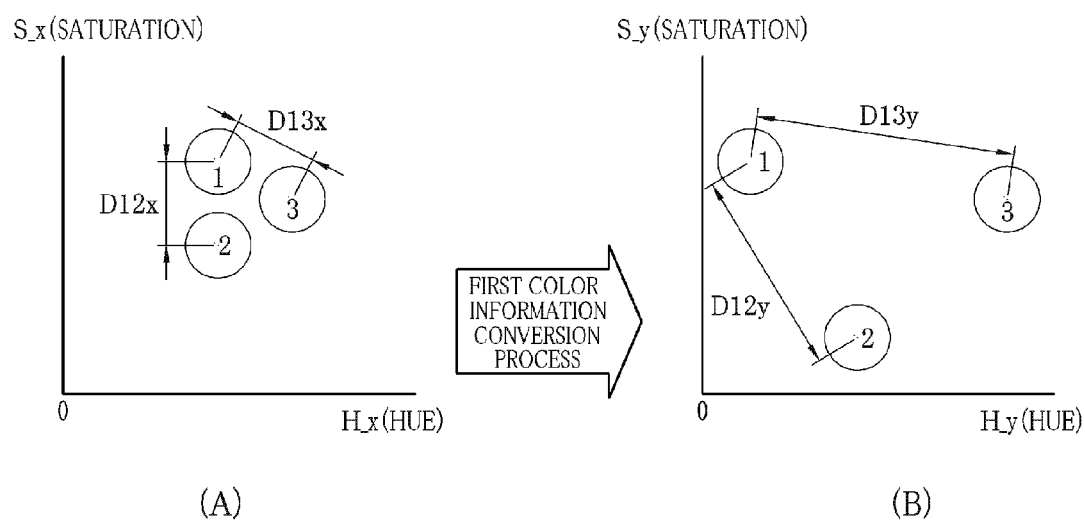
FIG. 35 is an explanatory view illustrating a first color information conversion process (for the HS space)

As illustrated in the part (A) of FIG. 35, the first to third observation areas are distributed in the first quadrant of a first HS space (which corresponds to the "first feature space" of the present invention) that is formed by the first saturation S_x (the vertical axis) and the first hue H_x (the horizontal axis). In the first HS space, there is a difference D12x between the first and second observation areas (for example, between the average value of the first observation area and the average value of the second observation area). There is a difference D13x between the first and third observation areas (for example, between the average value of the first observation area and the average value of the third observation area). The difference D12x represents a difference in saturation between colors in the first observation area and colors in the second observation area in the image. The difference D13x represents a difference in hue between the colors in the first observation area and colors in the third observation area in the image.

As illustrated in the part (B) of FIG. 35, the positions of the first to third observation areas in a second HS space differ from those in the first HS space. The second HS space is formed by the second saturation S_y (the vertical axis) and the second hue H_y (the horizontal axis), which are obtained by the first color information conversion process (for the HS space). In the second HS space (which corresponds to the "second feature space" of the present invention), there is a difference D12y between the first and second observation areas (for example, between the average value of the first observation area and the average value of the second observation area). There is a difference D13y between the first and third observation areas (for example, between the average value of the first observation area and the average value of the third observation area).

The difference D12y represents differences in saturation and hue between the colors in the first observation area and the colors in the second observation area in the image. The difference D12y is greater than the difference D12x. The difference D13y represents a difference in hue between the colors in the first observation area and the colors in the third observation area in the image. The difference D13y is greater than the difference D13x. Furthermore, the coordinates corresponding to the first observation area in the second HS space differ from the coordinates corresponding to the first observation area in the first HS space. In other words, at least one of the saturation and the hue of the first observation area after the first color information conversion process (for the HS space) differs from that before the first color information conversion process.

As described above, the first color information conversion process (for the HS space) increases the difference between the first and second observation areas and the difference between the first and third observation areas. Also, at least one of the saturation and the hue of the first observation area is changed by the first color information conversion process. The first special image is produced from the second hue H_y and the second saturation S_y, which have been subjected to the first color information conversion process (for the HS space), in a manner similar to the above.

Figure 36:
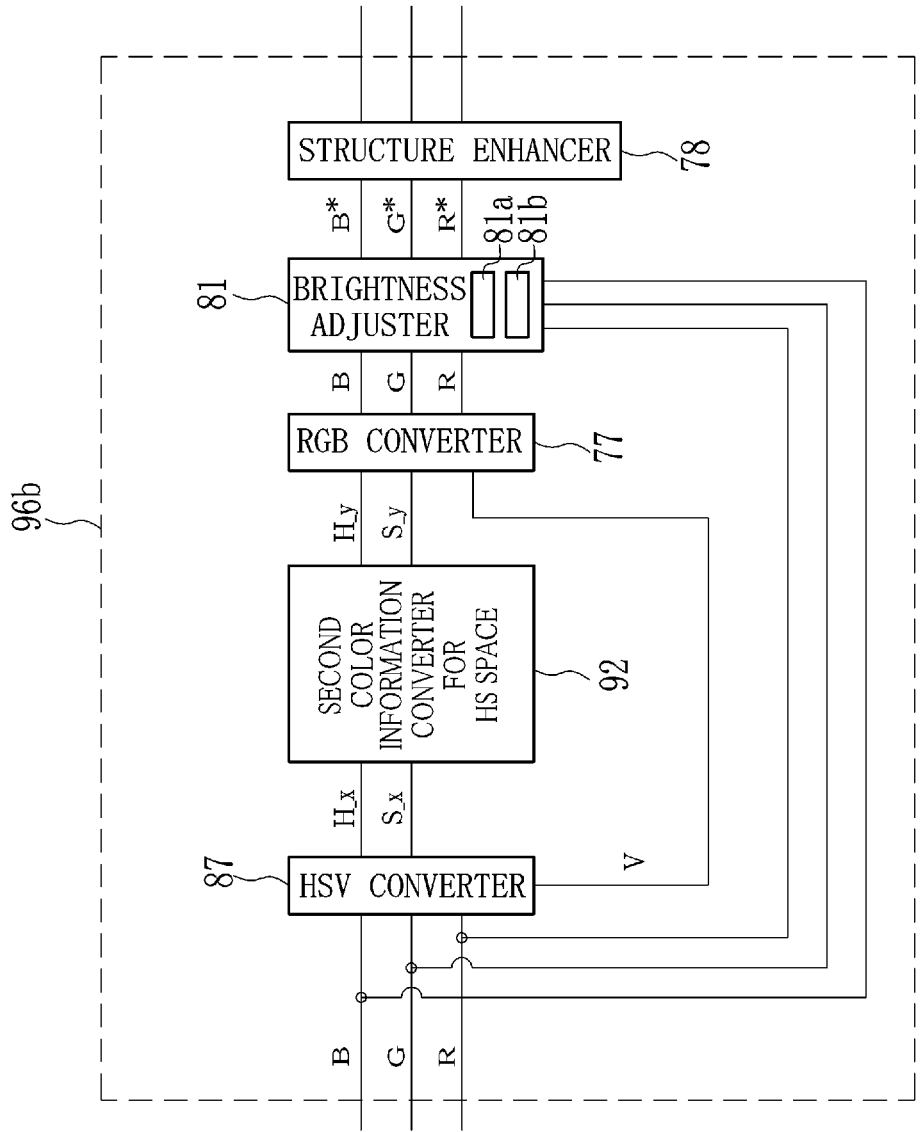
FIG. 36 is a block diagram illustrating functions of a second special image processor having a second color information converter (for the HS space)

A second special image processor 96b (see FIG. 36), which has substantially the same configuration as that of the first special image processor 96a, performs the second color information conversion process (for the HS space). The second special image processor 96b is the same as or similar to the first special image processor 96a except that the second special image processor 96b comprises a second color information converter 92 (for the HS space) in place of the first color information converter 88 (for the HS space).

The second color information converter 92 (for the HS space) performs the second color information conversion process (for the HS space) on the first hue H_x and the first saturation S_x to convert the first hue H_x and the first saturation S_x into the second hue H_y and the second saturation S_y. The second color information converter 92 (for the HS space) is composed of a two-dimensional LUT (Look Up Table), in which the first hue H_x, the first saturation S_x, the second hue H_y, and the second saturation S_y are stored in association with each other. The second hue H_y and the second saturation S_y are obtained by performing the second color information conversion process (for the HS space) based on the first hue H_x and the first saturation S_x. The second color information conversion process (for the HS space) will be detailed below.

Figure 37:
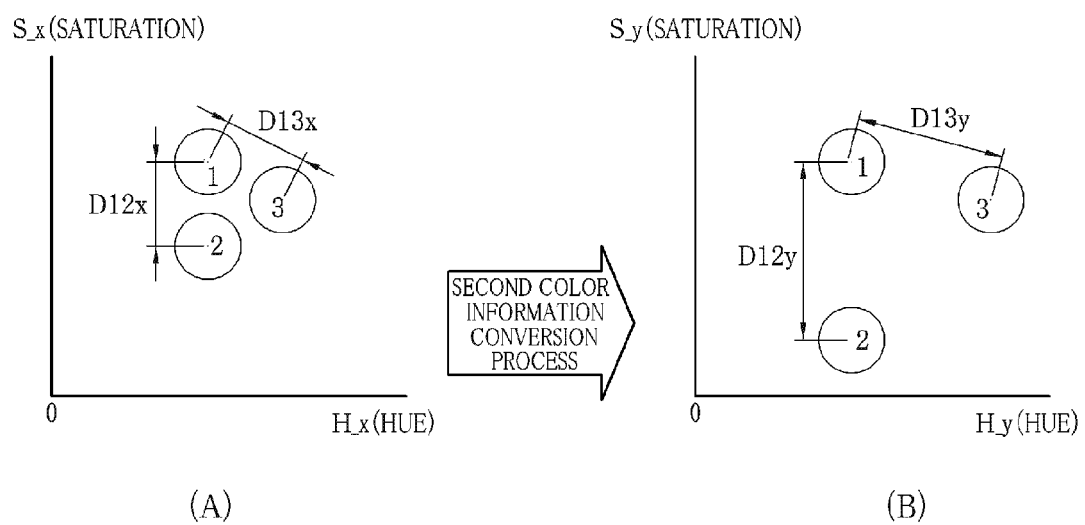
FIG. 37 is an explanatory view illustrating a second color information conversion process (for the HS space)

As illustrated in the part (A) of FIG. 37, the first, second, and third observation areas are distributed in the first quadrant of the first HS space, which is formed by the first saturation S_x (the vertical axis) and the first hue H_x (the horizontal axis). In the first HS space, there are difference D12x (difference in saturation) between the first and second observation areas and difference 13x (difference in hue) between the first and third observation areas. As illustrated in the part (B) of FIG. 37, the positions of the second and third observation areas, out of the first to third observation areas, in the second HS space differ from those in the first HS space. The second HS space is formed by the second hue H_y and the second saturation S_y, which are obtained by the second color information conversion process (for the HS space). In the second HS space, there is a difference D12y between the first and second observation areas. There is a difference D13y between the first and third observation areas.

The difference D12y represents a difference in saturation between the colors in the first observation area and the colors in the second observation area in the image. The difference D12y is greater than the difference D12x. The difference D13y represents a difference in hue between the colors in the first observation area and the colors in the third observation area in the image. The difference D13y is greater than the difference D13x. Furthermore, the coordinates corresponding to the first observation area in the second HS space are identical to the coordinates corresponding to the first observation area in the first HS space. In other words, the saturation and the hue of the first observation area before the second color information conversion process are identical to those of the first observation area after the second color information conversion process. As described above, the second color information conversion process (for the HS space) increases the difference between the first and second observation areas and the difference between the first and third observation areas while the saturation and the hue of the first observation area are maintained unchanged. Thus, the second special image is produced from the second hue H_y and the second saturation S_y, which have been subjected to the second color information conversion process (for the HS space) in a like manner.

Figure 38:
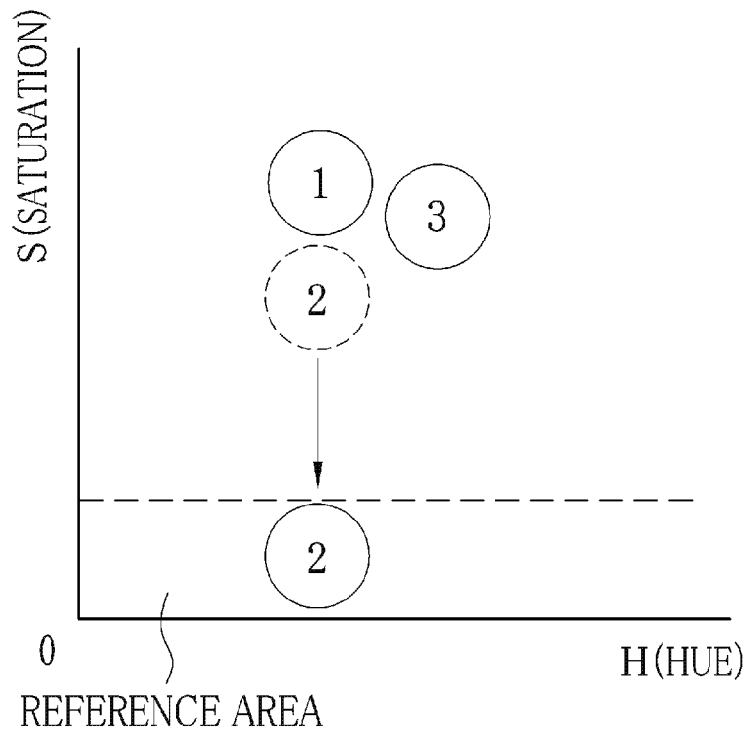
FIG. 38 is an explanatory view illustrating a first process (for the HS space)

The first color information conversion process (for the HS space) is composed of first and second processes (for the HS space). As illustrated in FIG. 38, in the first process, first, the coordinates which correspond to the second observation area are moved downward, in a parallel manner, in the saturation direction while the coordinates which correspond to the first observation area and the coordinates which correspond to the third observation areas are maintained unchanged. As a result of this parallel movement, the coordinates which correspond to the second observation area are moved to the inside of the reference area. The reference area is a region which contains the origin point of the first HS space and in which the saturation is low. The reference area excludes the first and third observation areas which have been subjected to the first process (for the HS space).

Figure 39:
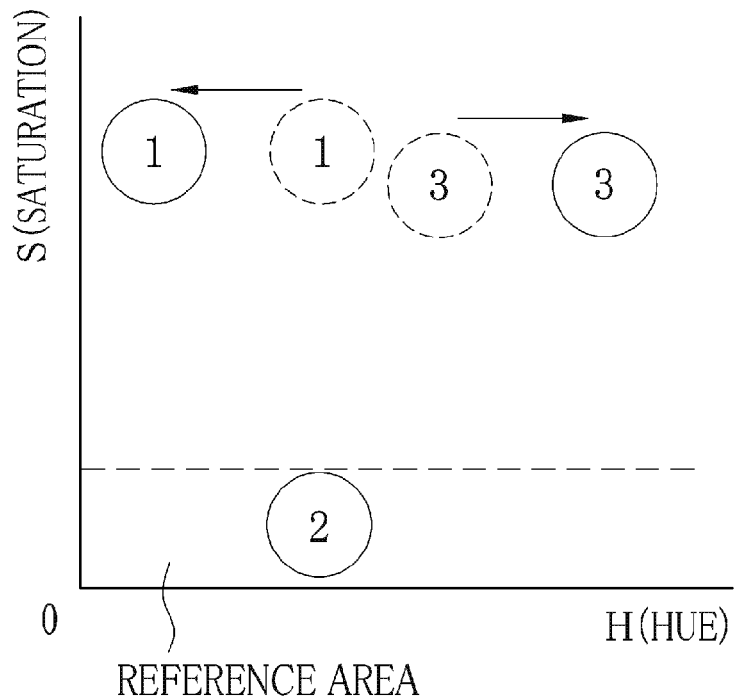
FIG. 39 is an explanatory view illustrating a second process (for the HS space)

As illustrated in FIG. 39, in the second process (for the HS space), the coordinates which correspond to the first observation area and the coordinates which correspond to the third observation area are moved, in a parallel manner, to be away from each other, out of the first to third observation areas which have been subjected to the first process (for the HS space) while the coordinates which correspond to the second observation area are maintained in the reference area. The coordinates which correspond to the first observation area are moved to the left, in a parallel manner, in the hue direction and the coordinates which correspond to the third observation area are moved to the right, in a parallel manner, in the hue direction.

Figure 40:
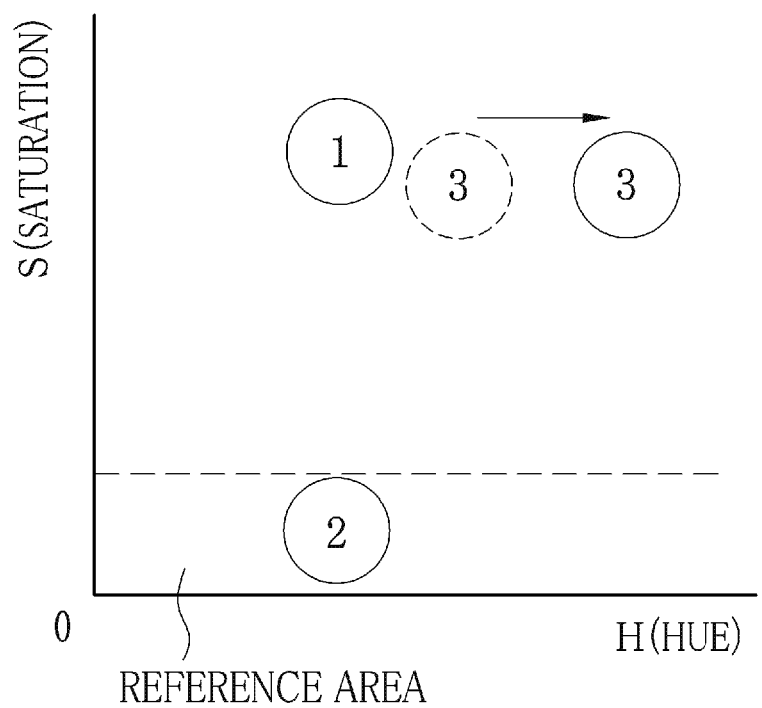
FIG. 40 is an explanatory view illustrating a third process (for the HS space)

The second color information conversion process (for the HS space) is composed of the first and third processes (for the HS space). The first process (for the HS space) is the same as or similar to the above. As illustrated in FIG. 40, with regard to the third process (for the HS space) performed after the first process (for the HS space), the coordinates which correspond to the third observation area are moved in a parallel manner to the right in the hue direction while the coordinates which correspond to the second observation area are maintained in the reference area and while the coordinates which correspond to the first observation area are maintained unchanged, out of the first to third observation areas which have been subjected to the first process (for the HS space).

Second Embodiment

In the second embodiment, the object is illuminated with lasers and a phosphor, instead of the LEDs 20a to 20d of the four colors described in the first embodiment. Other than those, the configuration is the same as or similar to that in the first embodiment.

Figure 41:
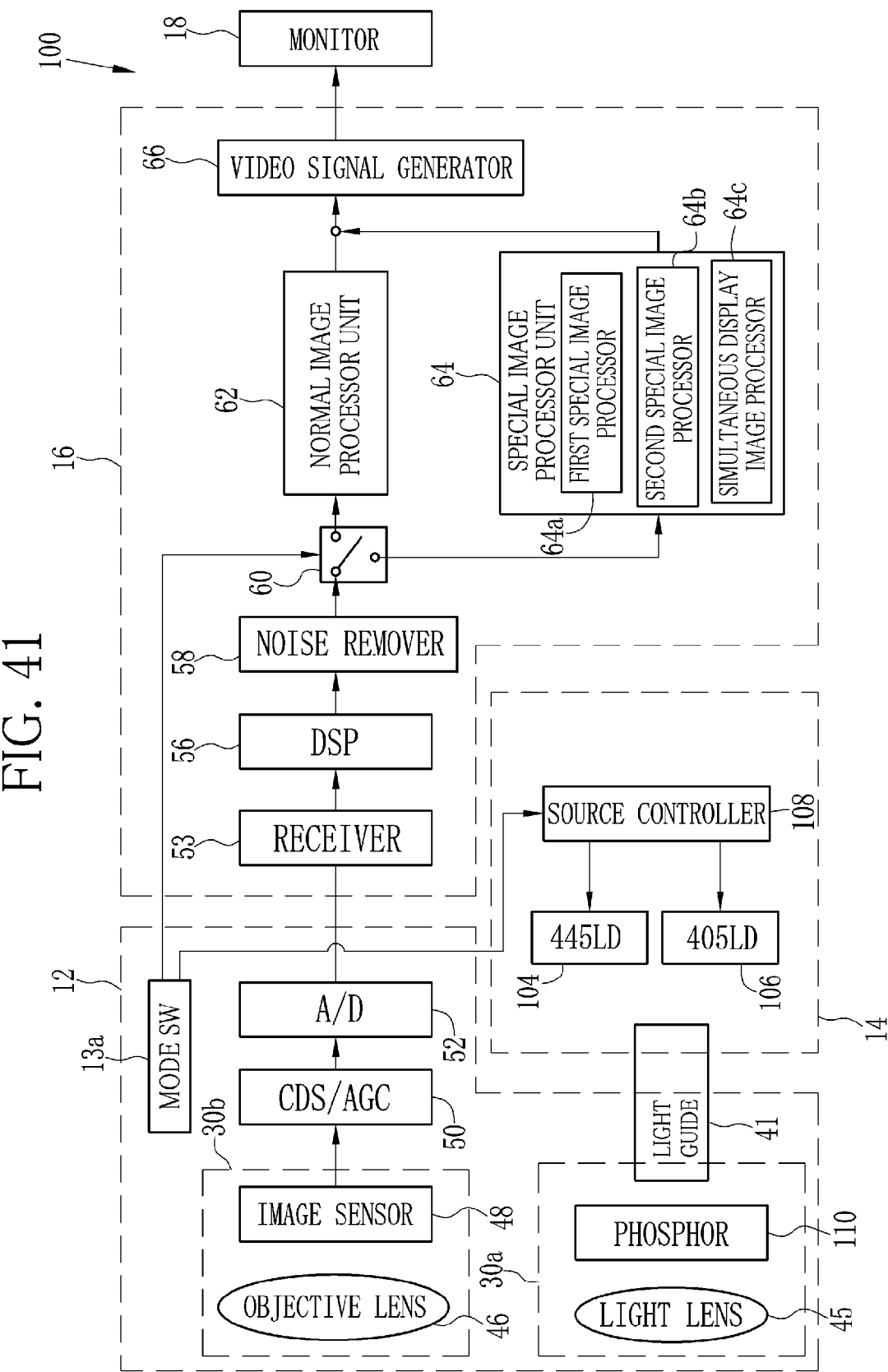
FIG. 41 is a block diagram illustrating functions of an endoscope system of a second embodiment.

As illustrated in FIG. 41, in the light source device 14 of an endoscope system 100 according to the second embodiment, a blue laser (denoted as 445LD in FIG. 41) 104 and a blue-violet laser (denoted as 405LD in FIG. 41) 106 are provided in place of the LEDs 20a to 20d of the four colors. The blue laser 104 emits blue laser beams with the center wavelength 445±10 nm. The blue-violet laser 106 emits blue-violet laser beams with the center wavelength 405±10 nm. The light emissions from the semiconductor light emitting elements of the lasers 104 and 106 are controlled independently by a source controller 108. The light quantity ratio between the light (laser beams) from the blue laser 104 and the light (laser beams) from the blue-violet laser 106 may be changed as desired.

In the normal mode, the source controller 108 actuates the blue laser 104. In the first special mode, the second special mode, or the simultaneous display mode, the source controller 108 actuates and controls both the blue laser 104 and the blue-violet laser 106 such that the light-emission intensity of the blue laser beams is greater than that of the blue-violet laser beams. The laser beams emitted from each of the lasers 104 and 106 are incident on the light guide (LG) 41 through optical members (e.g. a condenser lens, an optical fiber, a combiner, and the like, all not shown).

Note that a full width at half maximum of the blue laser beams or the blue-violet laser beams is preferred to be in the order of ±10 nm. Broad-area type InGaN-based laser diodes may be used as the blue laser 104 and blue-violet laser 106. The InGaNAs-based laser diodes and the GaNAs-based laser diodes may be used instead. A light emitting element such as a light emitting diode may be used as the light source.

The illumination optical system 30a is provided with the light lens 45 and a phosphor 110 on which the blue laser beams or the blue-violet laser beams from the light guide 41 are incident. The phosphor 110 emits fluorescence when irradiated with the blue laser beams. Apart of the blue laser beams passes through the phosphor 110. The blue-violet laser beams pass through the phosphor 110 without exciting the phosphor. The light from the phosphor 110 is applied to the object through the light lens 45.

Figure 42:
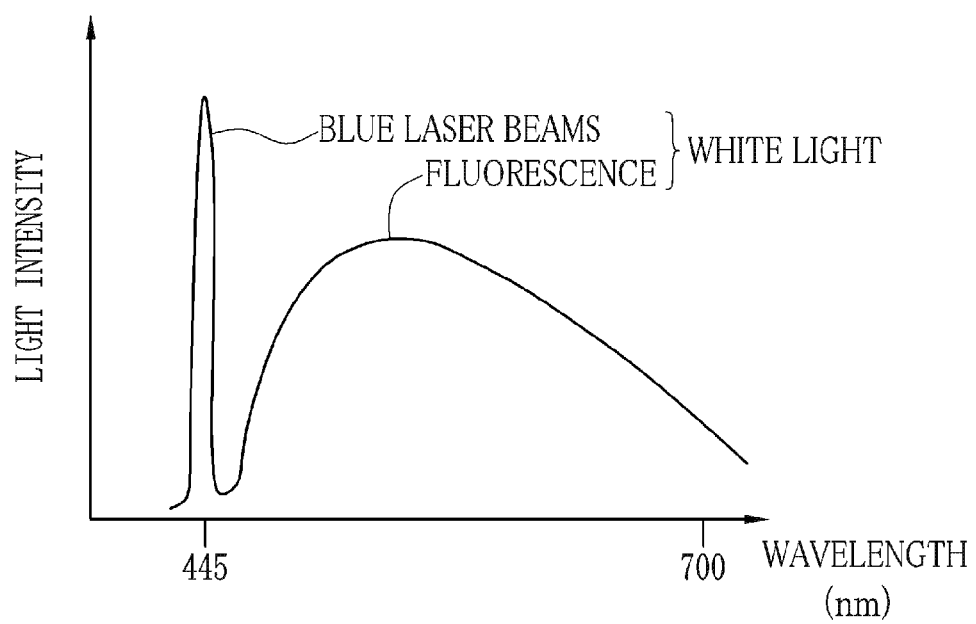
FIG. 42 is a graph illustrating an emission spectrum of white light.
Figure 43:
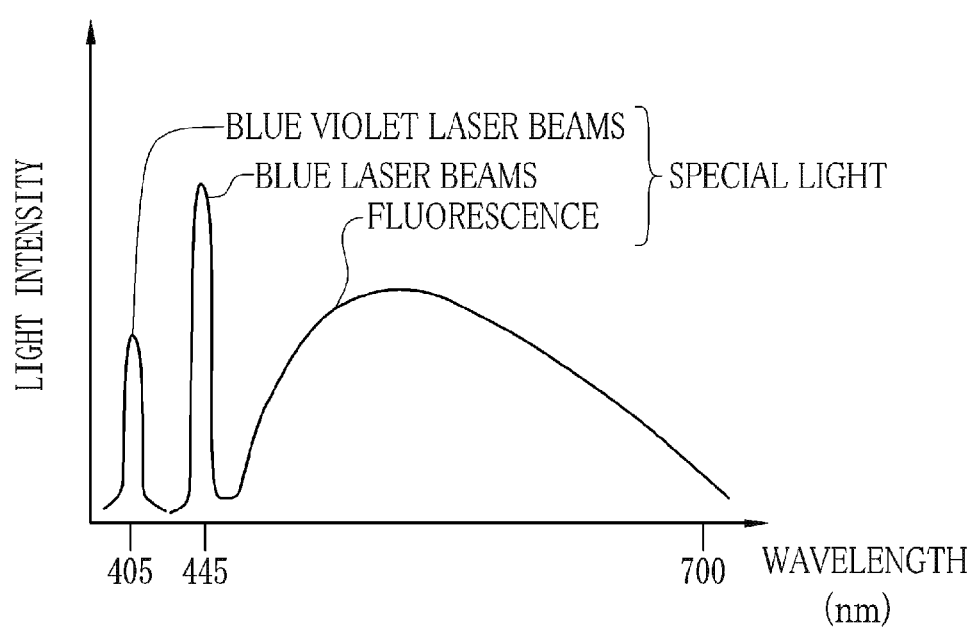
FIG. 43 is a graph illustrating an emission spectrum of special light.

Here, in the normal mode, the blue laser beams are mostly incident on the phosphor 110, so that white light, being the combination of the blue laser beams and the fluorescence from the phosphor 110 excited by the blue laser beams, is applied to the object as illustrated in FIG. 42. In the first special mode, the second special mode, or the simultaneous display mode, both the blue-violet laser beams and the blue laser beams are incident on the phosphor 110, so that the special light, being the combination of the blue-violet laser beams, the blue laser beams, and the fluorescence from the phosphor 110 excited by the blue laser beams, is applied to the object as illustrated in FIG. 43.

Note that it is preferred to use the phosphor 110 containing two or more types of phosphor components (e.g. YAG-based phosphor, BAM($BaMgAl_{10}O_{17}$), or the like) which absorb a part of the blue laser beams and emit light of green to yellow colors. In the case where the semiconductor light emitting elements are used as the excitation light sources for the phosphor 110 as described in this example, the high-intensity white light is provided with high light-emission efficiency, the intensity of the white light is controlled easily, and the variations in the color temperature and chromaticity of the white light are small.

Third Embodiment

In the third embodiment, instead of the LEDs 20a to 20d of the four colors described in the first embodiment, a broadband light source (e.g. a xenon lamp) and a rotary filter are used to illuminate the object. Instead of the color image sensor 48, a monochrome image sensor is used to image the object. The components other than those are the same as or similar to the components described in the first embodiment.

Figure 44:
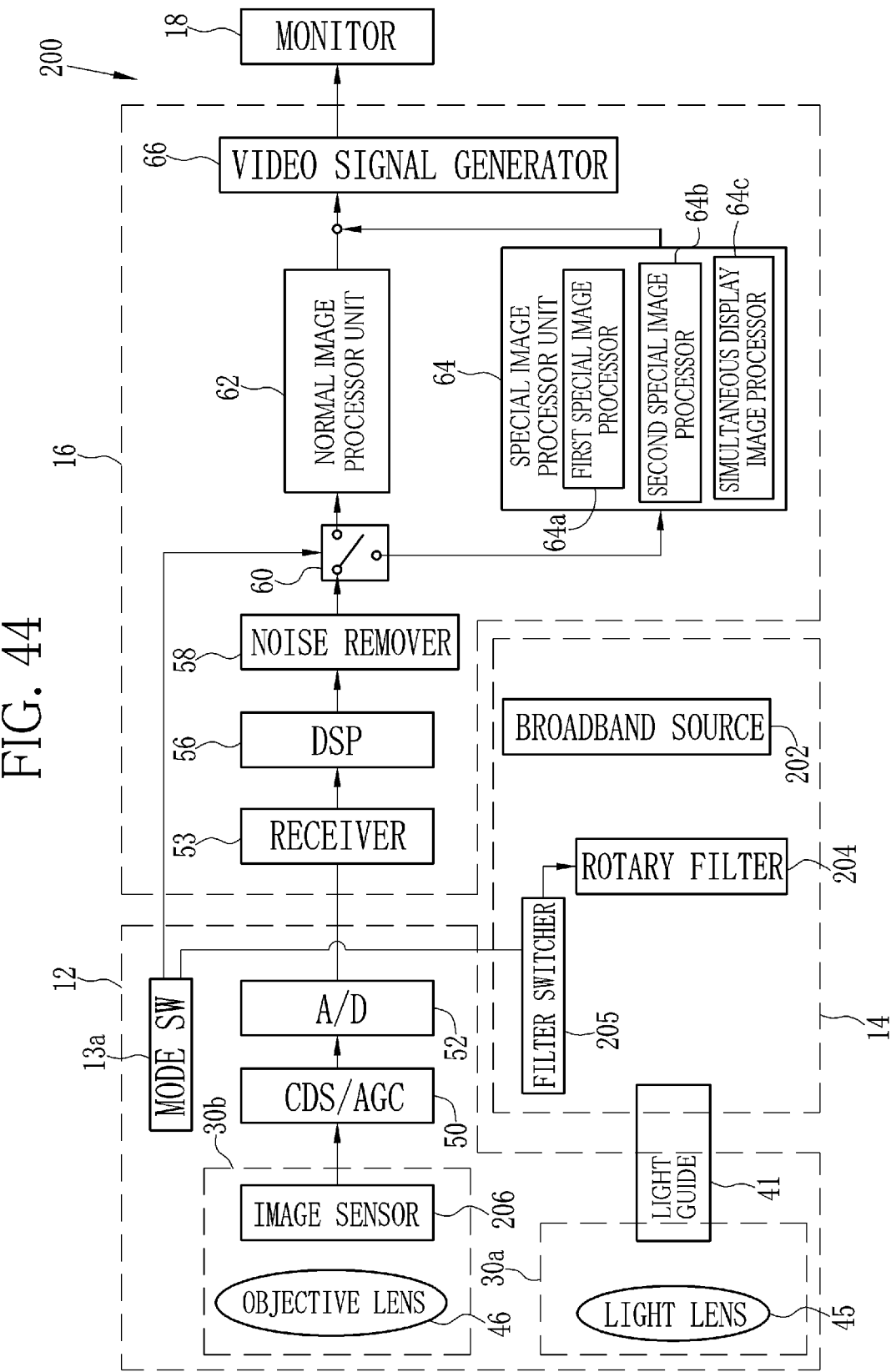
FIG. 44 is a block diagram illustrating functions of an endoscope system of a third embodiment.

As illustrated in FIG. 44, in an endoscope system 200 of the third embodiment, a broadband light source 202, a rotary filter 204, and a filter switcher 205 are provided instead of the LEDs 20a to 20d in the light source device 14. The imaging optical system 30b is provided with a monochrome image sensor 206 with no color filter, in place of the color image sensor 48.

The broadband light source 202 is composed of a xenon lamp, a white LED, or the like, and emits white light having the wavelength range from blue to red. The rotary filter 204 comprises a normal filter 208 provided on the inner side and a special filter 209 provided on the outer side (see FIG. 45). The filter switcher 205 shifts the rotary filter 204 in the radial direction. When the mode is set to the normal mode by the operation of the mode SW 13a, the normal filter 208 of the rotary filter 204 is inserted into the light path of the white light. When the mode is set to the first special mode, the second special mode, or the simultaneous display mode, the special filter 209 of the rotary filter 204 is inserted into the light path of the white light.

Figure 45:
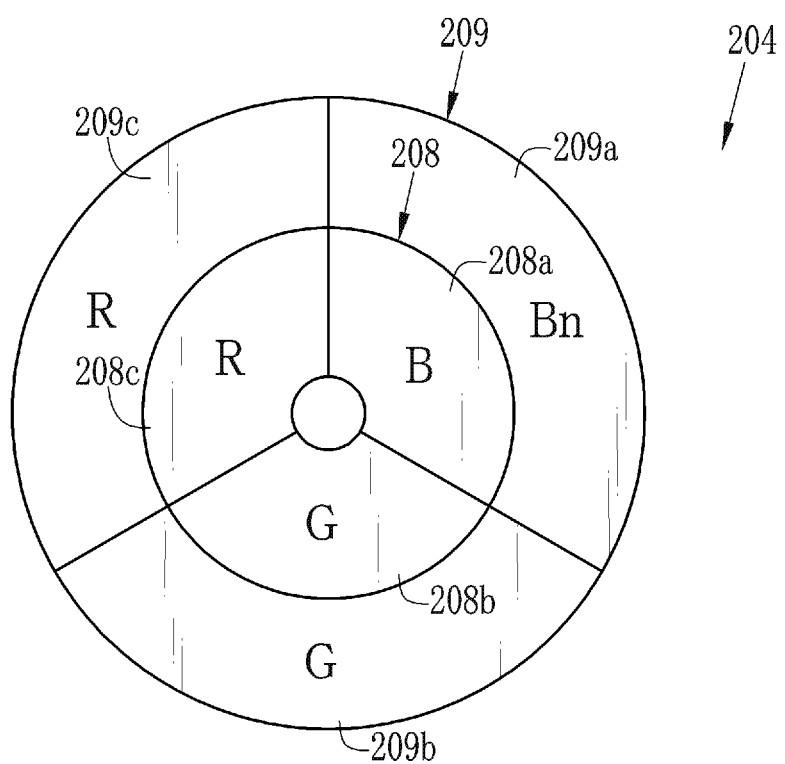
FIG. 45 is a plan view illustrating a rotary filter.

As illustrated in FIG. 45, the normal filter 208 comprises a B filter 208a, a G filter 208b, and an R filter 208c in the circumferential direction. The B filter 208a transmits the blue light of the white light. The G filter 208b transmits the green light of the white light. The R filter 208c transmits the red light of the white light. In the normal mode, the blue light, the green light, and the red light are applied in this order to the object as the rotary filter 204 is rotated.

The special filter 209 comprises a Bn filter 209a, a G filter 209b, and an R filter 209c in the circumferential direction. The Bn filter 209a transmits the blue narrowband light having a specific wavelength range of the white light. The G filter 209b transmits the green light of the white light. The R filter 209c transmits the red light of the white light. In the special mode, the blue narrowband light, the green light, and the red light are applied in this order to the object as the rotary filter 204 is rotated.

In the endoscope system 200, in the normal mode, the monochrome image sensor 206 takes an image of the object every time the blue light, the green light, or the red light is applied to the object. Thereby, the three colors (RGB) of image signals are obtained. The normal image is produced based on the RGB image signals in a manner the same as or similar to that in the first embodiment.

In the first special mode, the second special mode, or the simultaneous display mode, the monochrome image sensor 206 takes an image of the object every time the blue narrowband light, the green light, or the red light is applied to the object. Thereby, a Bn image signal, a G image signal, and an R image signal are obtained. The first or second special image is produced based on the Bn image signal, the G image signal, and the R image signal. The Bn image signal is used in place of the B image signal to produce the first or second special image. Other than that, the first or second special image is produced in a manner the same as or similar to that of the first embodiment.

Fourth Embodiment

In a fourth embodiment, a swallow-type capsule endoscope is used, instead of the insertion-type endoscope 12 and the light source device 14, to obtain the RGB image signals, which are necessary for producing the normal image, the first special image, or the second special image.

Figure 46:
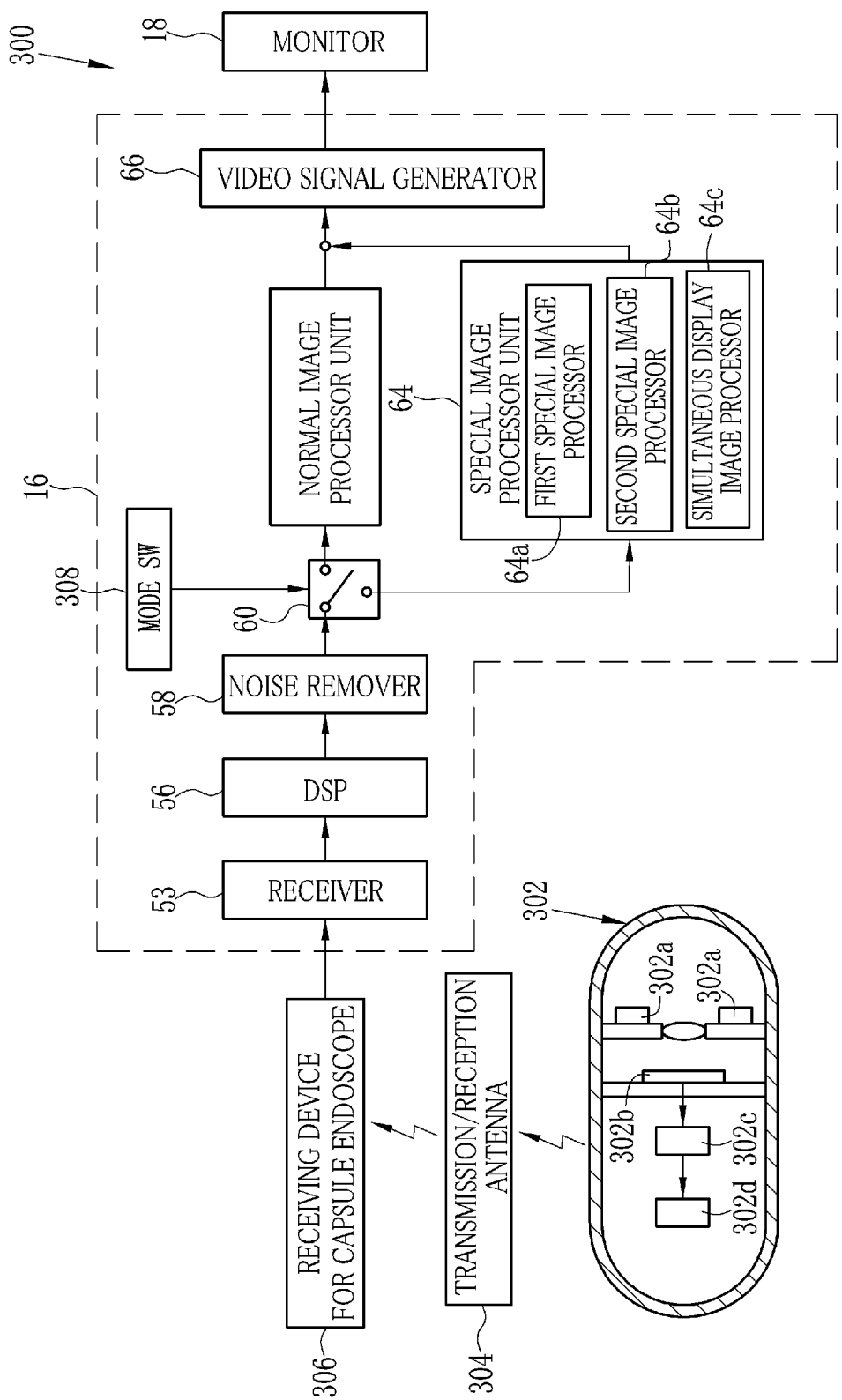
FIG. 46 illustrates functions of a capsule endoscope system of a fourth embodiment.

As illustrated in FIG. 46, a capsule endoscope system 300 according to the fourth embodiment comprises a capsule endoscope 302, a transmission/reception antenna 304, a receiving device 306 for the capsule endoscope 302, the processor device 16, and the monitor 18. The capsule endoscope 302 comprises LEDs 302a, an image sensor 302b, an image processor 302c, and a transmission antenna 302d. Note that the processor device 16 is the same as or similar to the one used in the first embodiment. In the fourth embodiment, a mode switch (SW) 308 is provided to switch among the normal mode, the first special mode, the second special mode, and the simultaneous display mode.

The LED 302a emits the white light. Inside the capsule endoscope 302, two or more LEDs 302a are provided. Here, it is preferred that the LED 302a is a white light LED which comprises a blue light source and a phosphor that converts wavelengths of light from the blue light source into fluorescence. An LD (laser diode) may be used instead of the LED. The object is illuminated with the white light from the LED 302a.

The image sensor 302b is a color image sensor. The image sensor 302b takes an image of the object illuminated with the white light and outputs the RGB image signals. Here, it is preferred that the image sensor 302b is a CCD (Charge Coupled Device) image sensor or a CMOS (Complementary Metal-Oxide Semiconductor) image sensor. In the image processor 302c, the RGB image signals outputted from the image sensor 302b are subjected to a process for converting them into signals which are to be transmitted through the transmission antenna 302d. The RGB image signals, which have passed through the image processor 302c, are transmitted wirelessly from the transmission antenna 302d to the transmission/reception antenna 304.

The transmission/reception antenna 304 is affixed to the subject's body, and receives the RGB image signals from the transmission antenna 302d. The transmission/reception antenna 304 wirelessly transmits the received RGB image signals to the receiving device 306 for the capsule endoscope 302. The receiving device 306 is connected to the receiver 53 of the processor device 16, and transmits the RGB image signals, which have been received from the transmission/reception antenna 304, to the receiver 53.

Figure 47:
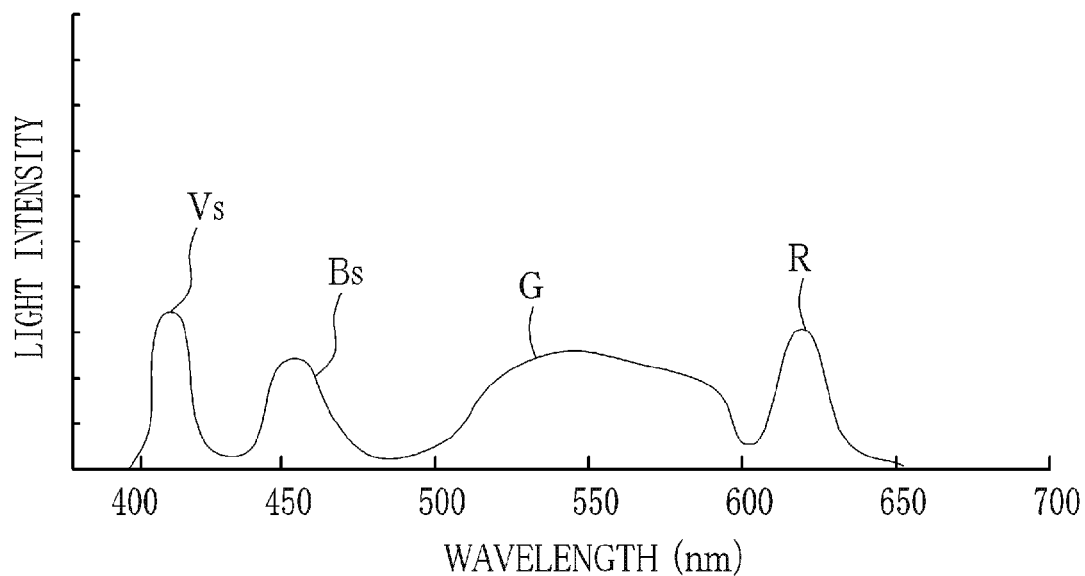
FIG. 47 is a graph illustrating emission spectrums of violet light V, blue light B, green light G, and red light R, which differ from those in FIG. 3.

Note that, in the above embodiments, the four colors of light with the emission spectrums illustrated in FIG. 3 are used by way of example. The emission spectrums are not limited to this example. For example, as illustrated in FIG. 47, the green light G and the red light R may have the same spectrums as those illustrated in FIG. 3. The violet light Vs may have the center wavelength 410 to 420 nm in a wavelength range slightly shifted to a longer wavelength side than that of the violet light V in FIG. 3. The blue light Bs may have the center wavelength 445 to 460 nm in a wavelength range slightly shifted to a shorter wavelength side than that of the blue light B in FIG. 3.

Note that, in the above embodiments, the angle θ is changed in the second process to move the first observation area and the third observation area away from each other. The first and third observation areas may be moved away from each other in a different way. For example, the radial coordinate r may be changed to move the first observation area and the third observation area away from each other. Both the radial coordinate r and the angle θ may be changed to move the first to third observation areas away from each other. In the second process, the coordinates corresponding to the first observation area may be changed (moved) while the coordinates corresponding to the third observation area are maintained unchanged.

Note that, in the above embodiments, the first B/G ratio and the first G/R ratio are obtained from the first RGB image signals. The first signal ratio space is formed by the first B/G ratio and the first G/R ratio. In the case where the first B image signal is a narrowband signal obtained from narrowband light (for example, the light with a full width at half maximum of 20 nm or less) having a narrow wavelength range, the difference (distance) between the first and second observation areas and the difference (distance) between the first and third observation areas in the first signal ratio space increase as compared with those of the case where the first B image signal is a broadband signal obtained from broadband light (for example, the light with a full width at half maximum of more than 20 nm) having a broad wavelength range. Here, the examples of the "narrowband light" includes the "violet light V" and the "blue light B" of the first embodiment, the "blue laser beams" and the "blue-violet laser beams" of the second embodiment, "the blue narrowband light" of the third embodiment, and the "light from the blue light source" of the fourth embodiment.

Figure 48:
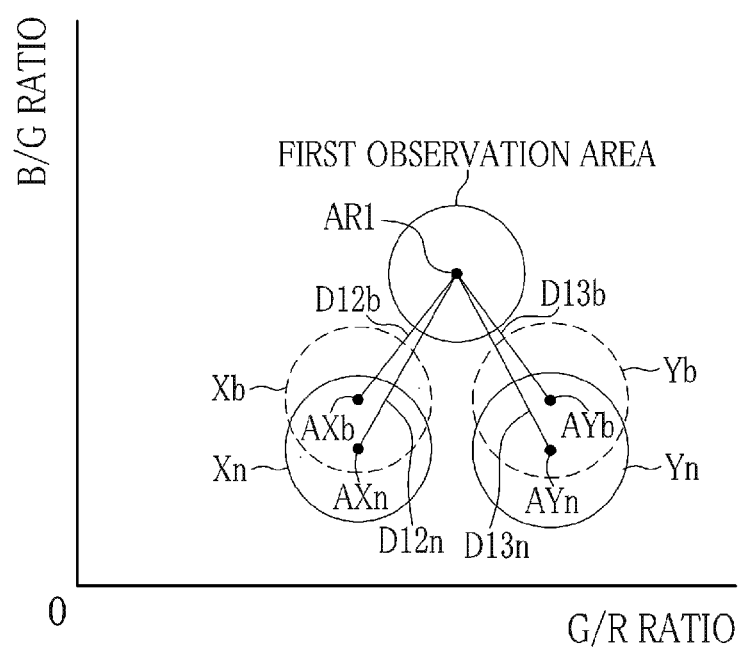
FIG. 48 is an explanatory view illustrating positions of the second and third observation areas in a first signal ratio space, for a case in which a first B image signal is a narrowband signal, and those in the first signal ratio space, for a case in which the first B image signal is a broadband signal.

In FIG. 48, "Xn" denotes the second observation area in the case where the first B image signal is the narrowband signal. "Xb" denotes the second observation area in the case where the first B image signal is the broadband signal. "Xn" is located lower than the "Xb" in the first signal ratio space. "Yn" denotes the third observation area in the case where the first B image signal is the narrowband signal. "Yb" denotes the third observation area in the case where the first B image signal is the broadband signal. "Yn" is located lower than the "Yb" in the first signal ratio space.

As illustrated in FIG. 48, the difference D12n between the average value AXn of "Xn" and the average value AR1 of the first observation area is greater than the difference D12b between the average value AXb of "Xb" and the average value AR1 of the first observation area. The difference D13n between the average value AYn of "Yn" and the average value AR1 of the first observation area is greater than the difference D13b between the average AYb of "Yb" and the average value AR1 of the first observation area. As described above, in the case where the first B image signal is a narrowband signal, the difference between the first and second observation areas and the difference between the first and third observation areas are significant even before the process for expanding and compressing a radial coordinate or an angle. The difference in color between the normal portion and the atrophic portion is displayed more clearly by performing the first or second color information conversion process (for the specific feature space) on the first to third observation areas which are already distant from each other.

Note that, in the case where the first G image signal is a narrowband signal, the difference between the first observation area and the second observation area and the difference between the first observation area and the third observation area are greater than those of the case where the first G image signal is a broadband signal, in a manner similar to the above. The narrowband signal is not limited to the first B image signal or the first G image signal described above. In the case where at least one of the first RGB image signals is a narrowband signal, the difference between the first and second observation areas and the difference between the first and third observation areas are greater than those of the case where all of the first RGB image signals are broadband signals. The examples of the "narrowband signal" include the above-described signal obtained from the narrowband light and a signal obtained by a spectral estimation process described in Japanese Patent Laid-Open Publication No. 2003-93336.

Note that the present invention is applicable to various types of medical image processing devices in addition to the processor devices incorporated in the endoscope systems described in the first to third embodiments and the capsule endoscope system described in the fourth embodiment.

Various changes and modifications are possible in the present invention and may be understood to be within the present invention.

What is claimed is:

1. A medical image processing device comprising:
an input processing unit for performing an input process of a first color image signal;
a color information obtaining section for obtaining two or more pieces of first color information from the first color image signal; and
a color information converter for performing a color information conversion process to convert the two or more pieces of first color information into two or more pieces of second color information, the color information conversion process making a difference $D12y$ greater than a difference $D12x$ and making a difference $13y$ greater than a difference $13x$, the difference $D12x$ being a difference between a first observation area and a second observation area that differs in position from the first observation area in a first feature space formed by the two or more pieces of first color information, the difference $D12y$ being a difference between the first and second observation areas in a second feature space formed by the two or more pieces of second color information, the difference $D13x$ being a difference between the first observation area and a third observation area that differs in position from the first and second observation areas in the first feature space, the difference $D13y$ being a difference between the first and third observation areas in the second feature space.

2. The medical image processing device according to claim 1, wherein the color information converter has a first color information converter for performing a first color information conversion process as the color information conversion process, and the first color information conversion process makes at least one of saturation and hue of the first observation area in the second feature space different from at least one of saturation and hue of the first observation area in the first feature space.

3. The medical image processing device according to claim 2, wherein the difference D12x before the first color information conversion process represents a difference in saturation, and the difference D13x before the first color information conversion process represents a difference in hue, and the difference D12y after the first color information conversion process represents differences in saturation and hue, and the difference D13y after the first color information conversion process represents a difference in hue.

4. The medical image processing device according to claim 2, wherein the color information converter has a second color information converter for performing a second color information conversion process as the color information conversion process, and the second color information conversion process makes the first observation area in the second feature space identical in saturation and hue to the first observation area in the first feature space.

5. The medical image processing device according to claim 4, wherein the difference D12x before the second color information conversion process represents a difference in saturation, and the difference D13x before the second color information conversion process represents a difference in hue, the difference D12y after the second color information conversion process represents a difference in saturation, and the difference D13y after the second color information conversion process represents a difference in hue.

6. An endoscope system comprising:
the medical image processing device according to claim 4; and
a display section for displaying a first special image and a second special image, the first special image being produced based on the two or more pieces of second color information obtained by the first color information conversion process, the second special image being produced based on the two or more pieces of second color information obtained by the second color information conversion process.

7. The medical image processing device according to claim 1, wherein the first color image signal is image signals of three colors, and the two or more pieces of first color information are a first signal ratio Mx, between the two image signals out of the image signals of three colors, and a first signal ratio Nx, between the two image signals out of the image signals of three colors, different from the first signal ratio Mx, and the color information converter performs the color information conversion process to convert the first signal ratio Mx and the first signal ratio Nx into a second signal ratio My and a second signal ratio Ny, being the two or more pieces of second color information.

8. The medical image processing device according to claim 1, wherein the two or more pieces of first color information are first color difference signals Cr_x and Cb_x, and the color information converter performs the color information conversion process to convert the first color difference signals Cr_x and Cb_x into second color difference signals Cr_y and Cb_y, being the two or more pieces of second color information.

9. The medical image processing device according to claim 1, wherein the two or more pieces of first color information are first components a*_x and b*_x, being color components in a CIE Lab space, and the color information converter performs the color information conversion process to convert the first components a*_x and b*_x into second components a*_y and b*_y, being the two or more pieces of second color information.

10. The medical image processing device according to claim 1, wherein the two or more pieces of first color information are a first hue H_x and a first saturation S_x, and the color information converter performs the color information conversion process to convert the first hue H_x and the first saturation S_x into a second hue H_y and a second saturation S_y, being the two or more pieces of second color information.

11. The medical image processing device according to claim 1, further comprising:
a color image signal converter for converting the two or more pieces of second color information into a second color image signal; and
a brightness adjuster for adjusting a pixel value of the second color image signal based on first brightness information obtained from the first color image signal and second brightness information obtained from the second color image signal.

12. The medical image processing device according to claim 1, wherein the first color image signal is image signals of three colors, and a difference D12n between the first and second observation areas in the first feature space, for a case in which at least one of the image signals is a narrowband signal, is greater than a difference D12b between the first and second observation areas in the first feature space, for a case in which all of the image signals are broadband signals, or a difference D13n between the first and third observation areas in the first feature space, for the case in which at least one of the image signals is a narrowband signal, is greater than a difference D13b between the first and third observation areas in the first feature space, for the case in which all of the image signals are broadband signals.

13. A method for operating a medical image processing device comprising the steps of:
performing an input process of a first color image signal with an input processing unit;
obtaining two or more pieces of first color information from the first color image signal, with a color information obtaining section; and
performing a color information conversion process to convert the two or more pieces of first color information into two or more pieces of second color information with a color information converter, the color information conversion process making a difference D12y greater than a difference D12x and making a difference 13y greater than a difference 13x, the difference D12x being a difference between a first observation area and a second observation area that differs in position from the first observation area in a first feature space formed by the two or more pieces of first color information, the difference D12y being a difference between the first and second observation areas in a second feature space formed by the two or more pieces of second color information, the difference D13x being a difference between the first observation area and a third observation area that differs in position from the first and second observation areas in the first feature space, the difference D13y being a difference between the first and third observation areas in the second feature space.

* * * * *